United States Patent
Plaβky et al.

(10) Patent No.: US 8,303,596 B2
(45) Date of Patent: Nov. 6, 2012

(54) METHOD AND DEVICE FOR POSITIONING OR ATTACHING A MEDICAL OPERATING INSTRUMENT, ESPECIALLY AN INCISION BLOCK OR A CUTTING BLOCK

(75) Inventors: Norman Plaβky, Erfurt (DE); Manuel Millahn, München (DE)

(73) Assignee: Brainlab AG, Feldkirchen (DE)

( * ) Notice: Subject to any disclaimer, the term of this patent is extended or adjusted under 35 U.S.C. 154(b) by 535 days.

(21) Appl. No.: 12/498,385

(22) Filed: Jul. 7, 2009

(65) Prior Publication Data
US 2010/0016859 A1 Jan. 21, 2010

Related U.S. Application Data

(60) Provisional application No. 61/078,481, filed on Jul. 7, 2008.

(30) Foreign Application Priority Data

Jul. 7, 2008 (EP) .................................. 08159784

(51) Int. Cl.
*A61B 17/58* (2006.01)
(52) U.S. Cl. ......................................................... 606/87
(58) Field of Classification Search ................ 606/86 R, 606/87, 88, 89, 130
See application file for complete search history.

(56) References Cited

U.S. PATENT DOCUMENTS

| | | | |
|---|---|---|---|
| 6,491,699 B1* | 12/2002 | Henderson et al. | 606/130 |
| 7,993,353 B2* | 8/2011 | Roβner et al. | 606/130 |
| 2002/0007188 A1* | 1/2002 | Arambula et al. | 606/130 |
| 2002/0038085 A1 | 3/2002 | Immerz | |
| 2002/0198531 A1 | 12/2002 | Millard et al. | |
| 2004/0039395 A1 | 2/2004 | Coon et al. | |
| 2005/0149041 A1* | 7/2005 | McGinley et al. | 606/88 |
| 2006/0235290 A1 | 10/2006 | Gabriel et al. | |

FOREIGN PATENT DOCUMENTS

| | | |
|---|---|---|
| DE | 103 09 493 | 9/2004 |
| EP | 1 574 170 | 9/2005 |
| EP | 1 690 503 | 8/2006 |

* cited by examiner

*Primary Examiner* — Kevin T Truong
*Assistant Examiner* — Christian Sevilla
(74) *Attorney, Agent, or Firm* — Renner, Otto, Boiselle & Sklar, LLP

(57) ABSTRACT

The present invention relates to a device for positioning a jig at a structure using at least one fixing element comprising at least one adjusting element which can directly interact with or guide the at least one fixing element and which can interact with the jig, so that the relative position between the at least one fixing element and the jig can be adjusted by changing the position of the at least one adjusting element, as well as to a method for positioning a jig at a structure comprising two rotatable adjusting elements, wherein the resection plane of the jig can be moved along or in a first direction when the adjusting elements are moved in the same direction and wherein the resection plane is turned if the adjusting elements are moved in an opposite or different direction or only one adjusting element is moved.

7 Claims, 23 Drawing Sheets

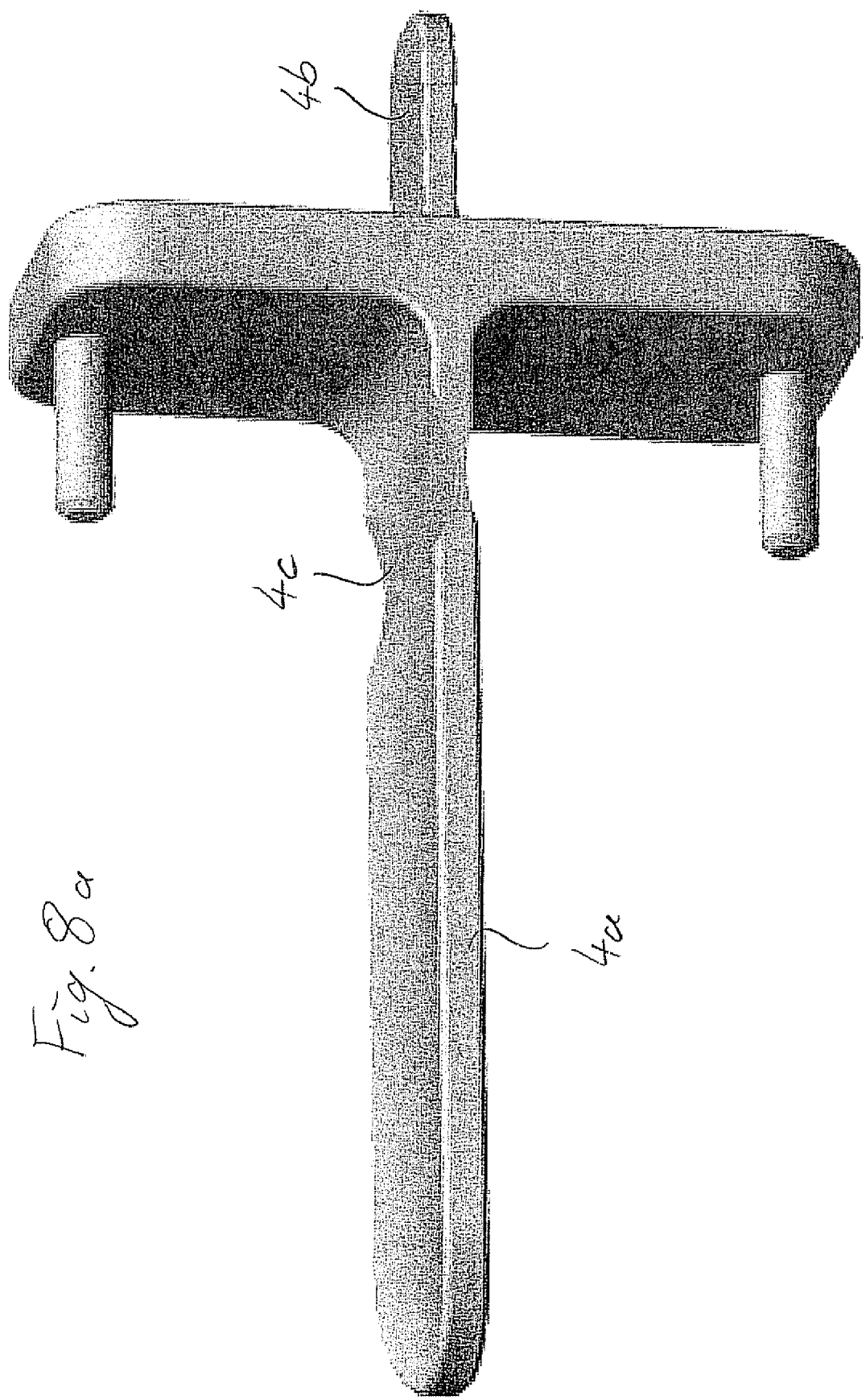

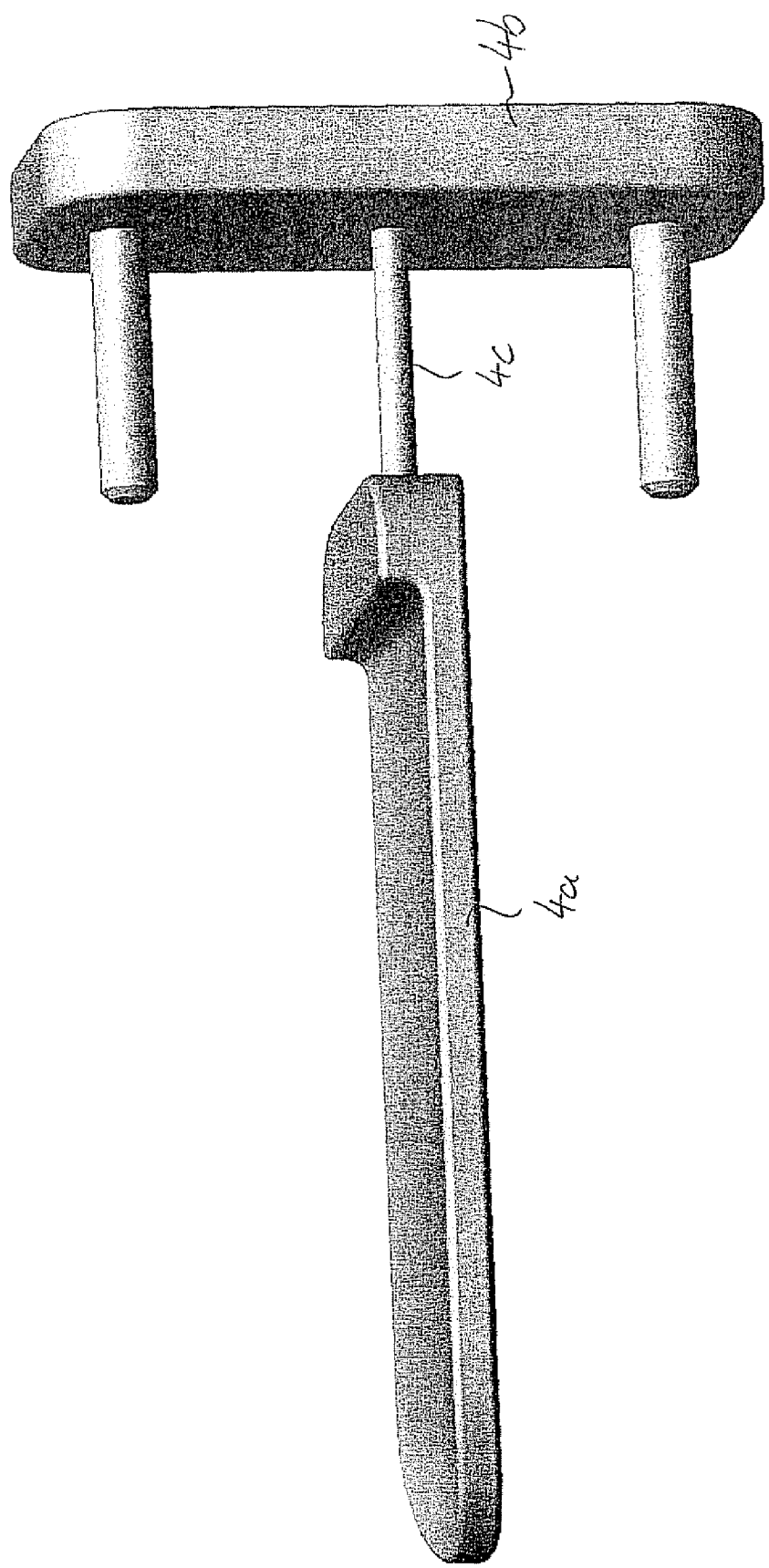

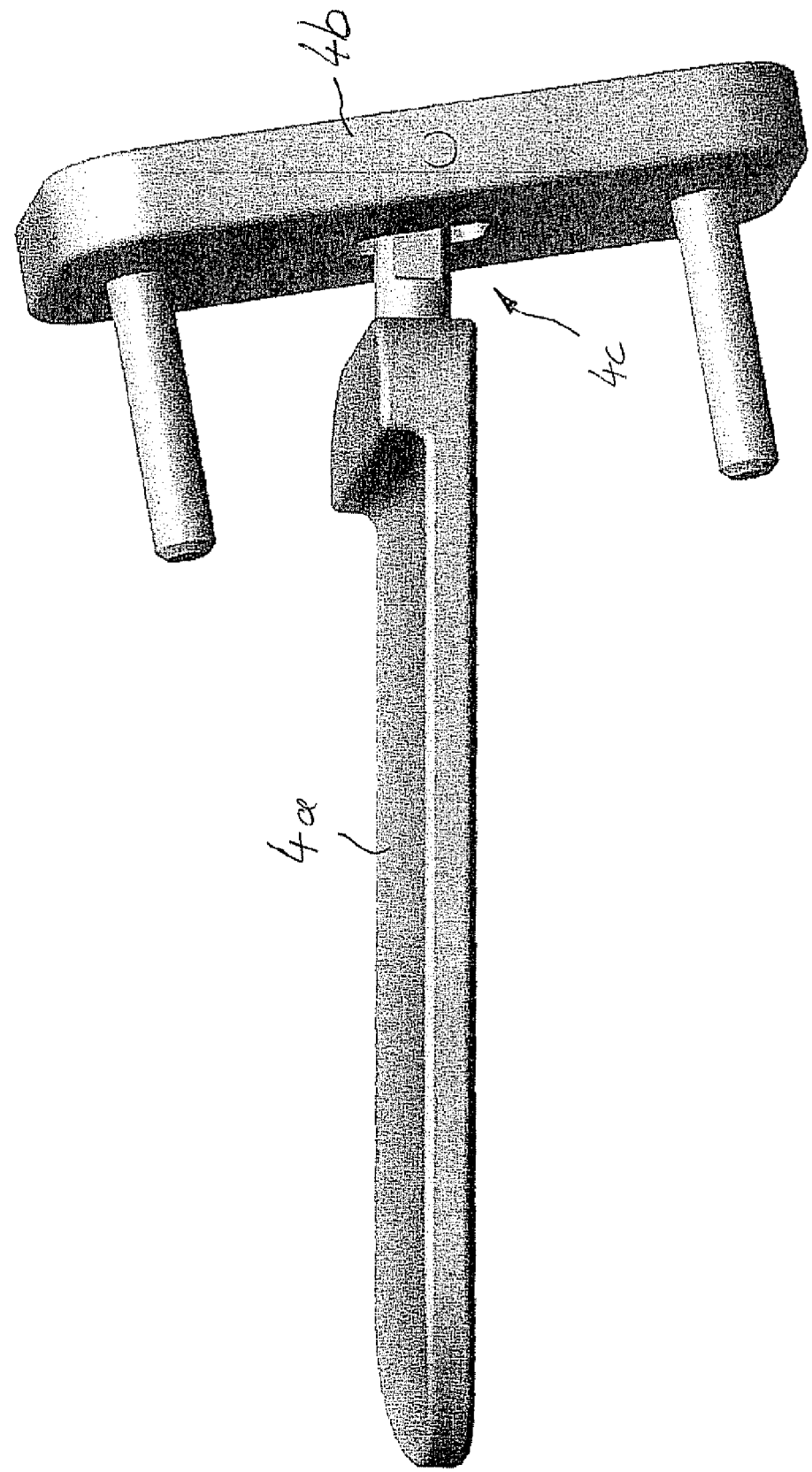

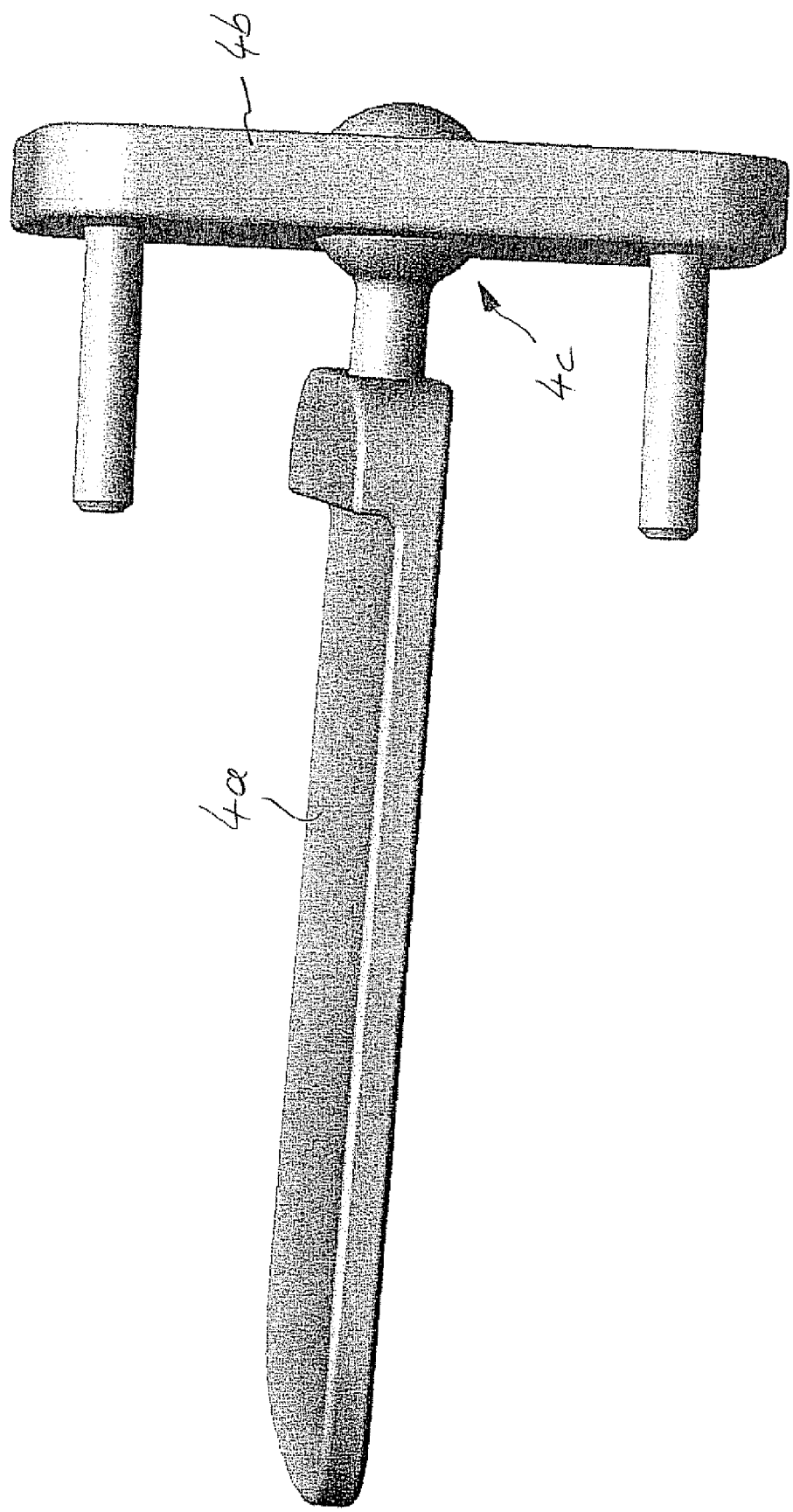

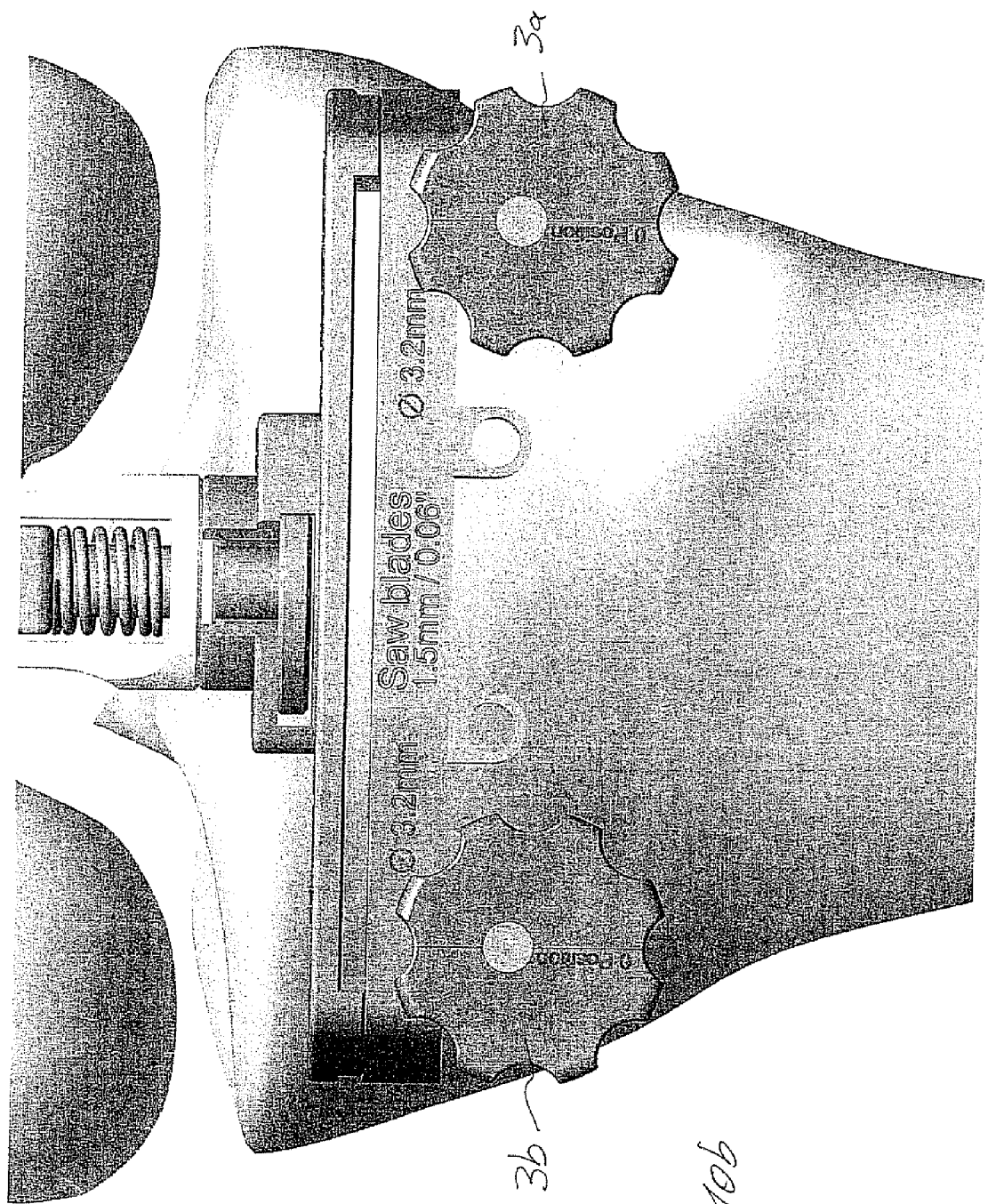

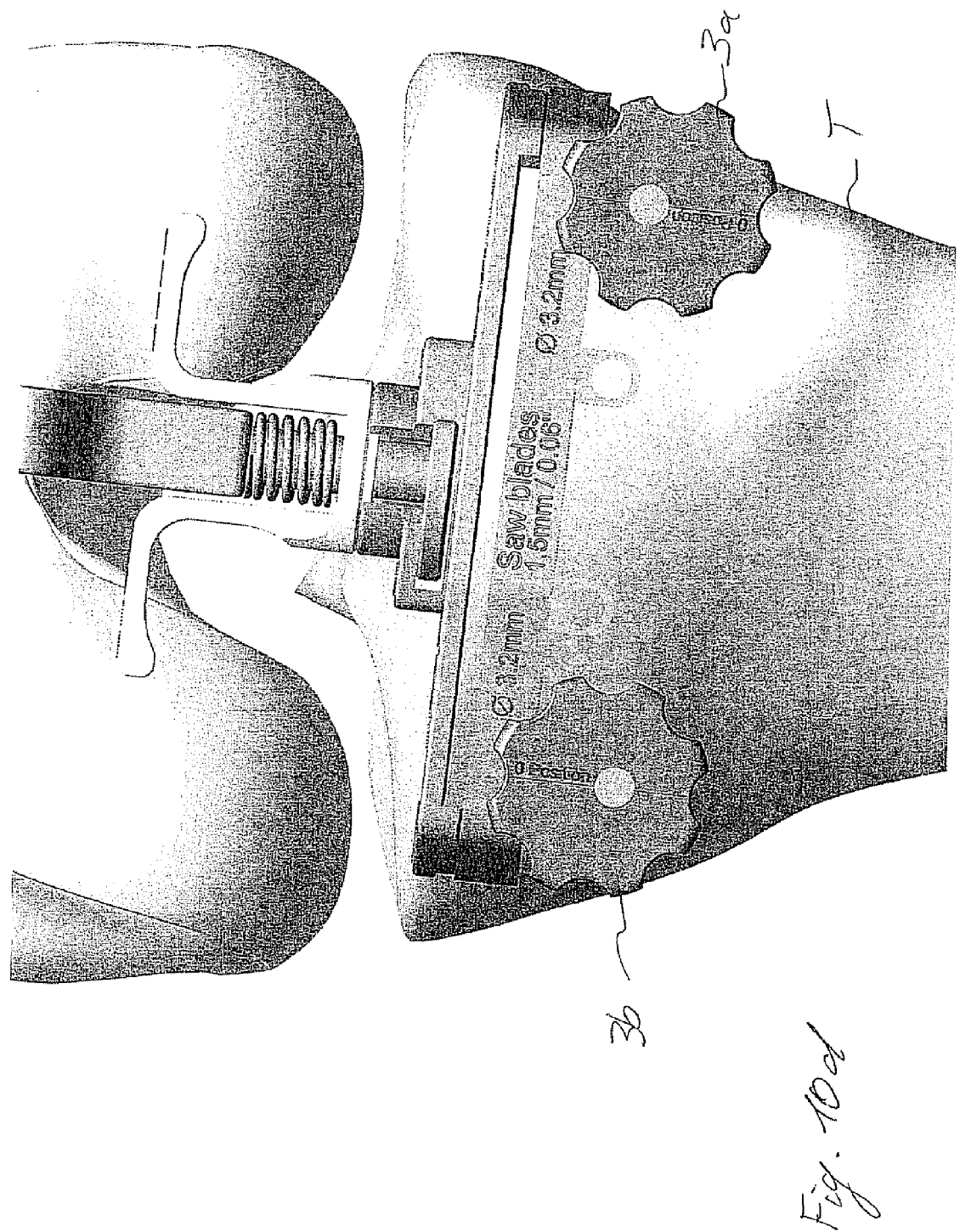

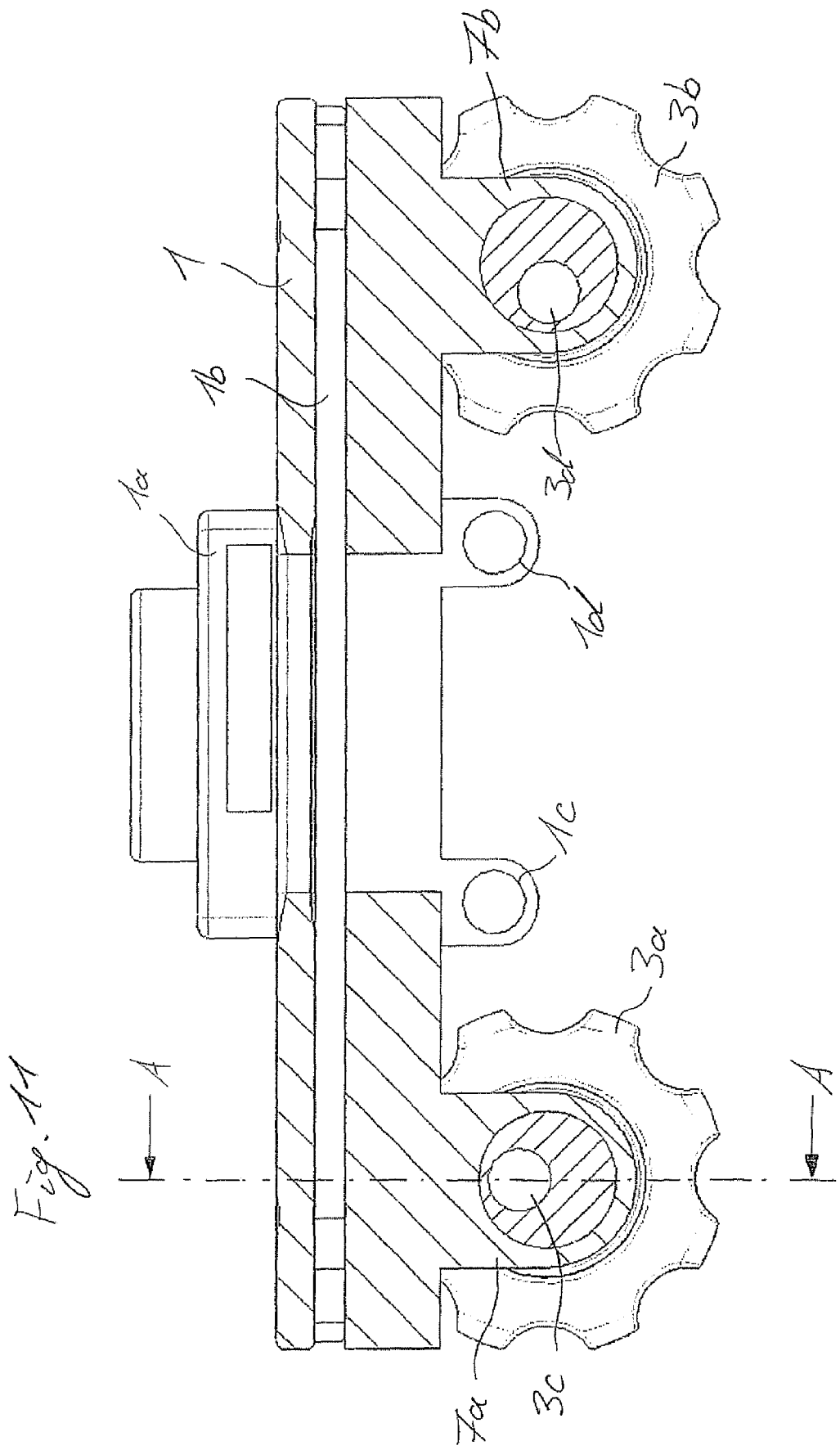

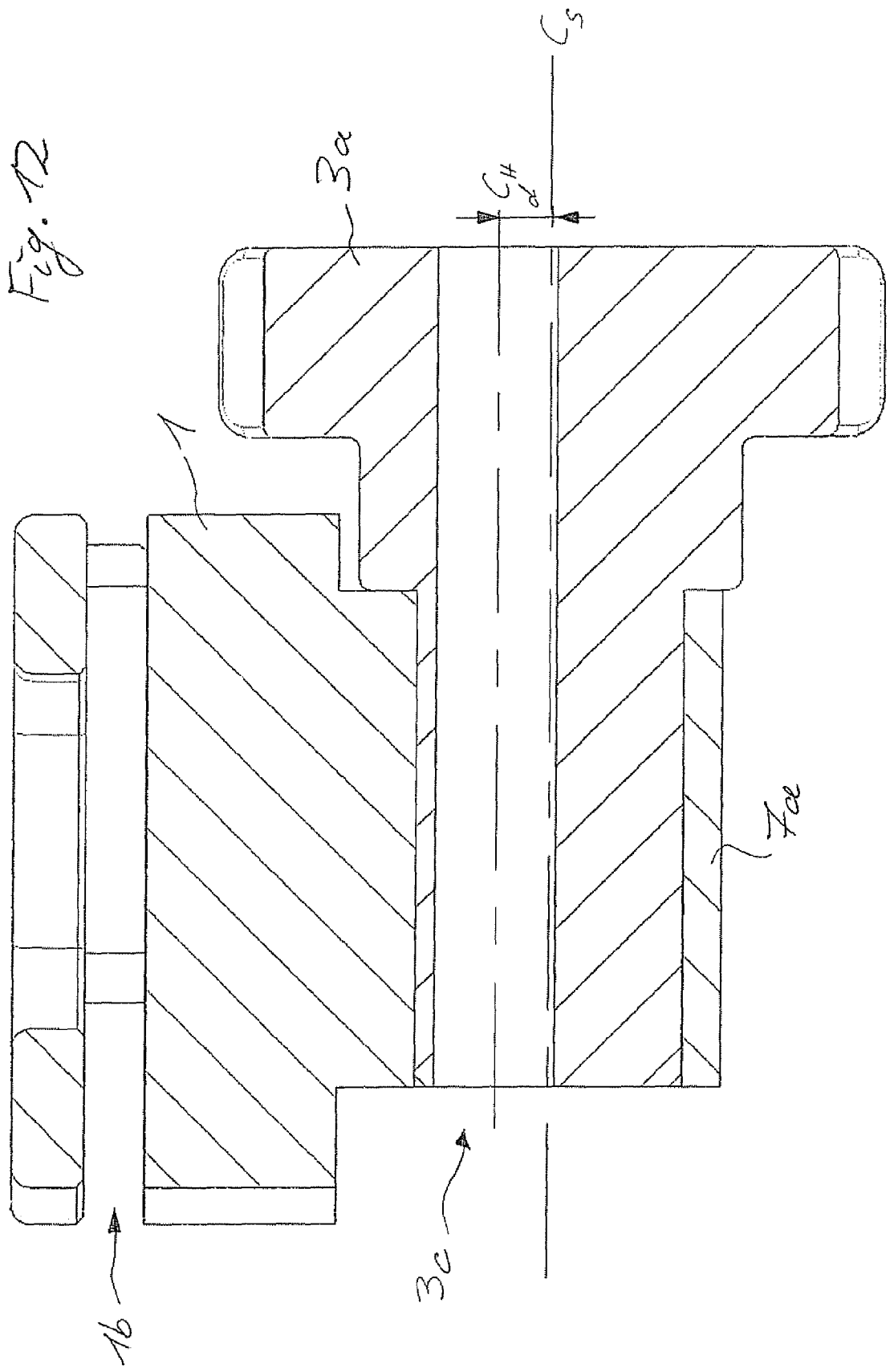

METHOD AND DEVICE FOR POSITIONING OR ATTACHING A MEDICAL OPERATING INSTRUMENT, ESPECIALLY AN INCISION BLOCK OR A CUTTING BLOCK

RELATED APPLICATION DATA

This application claims the priority of U.S. Provisional Application No. 61/078,481, filed on Jul. 7, 2008, which is hereby incorporated in its entirety by reference.

FIELD OF THE INVENTION

The present invention relates to a method and device for positioning or attaching an operating instrument, such as an incision block, a cutting block or a ligament balancing device, relative to a joint or a (bone) structure, such as e.g. femur or tibia.

The use of cutting blocks or jigs is known in implanting artificial knee joints. These jigs are attached to the femur and/or to the tibia to determine the incision planes of each bone for substantially defining the alignment of the femur and tibia implants. In this arrangement the jigs should as far as possible be positioned exactly using for example planning data such that after siting the implants, the mechanical femur axis and mechanical tibia axis are aligned with one another. Especially in navigated knee surgery the accuracy with which the cutting planes can be determined is of importance. Thus, a guided cutting jig is required which can preferably be adjusted during placement.

BACKGROUND OF THE INVENTION

When attaching implants, such as artificial knee, elbow, finger or hip joints, it is required that the implant, such as a joint or a part of a bone, is positioned as accurately as possible onto the adjacent bone. For this, the most accurate possible incisions must be made to the bone structures adjacent to the joint.

EP 07 102 301.4 of the applicant filed on Feb. 13, 2007 discloses a positioning device for aligning or positioning a device at a bone comprising a positioning tool and a positioning element having at least one base holding part, to which at least one device or base can detachably be attached.

EP 1 574 170 B1 of the applicant discloses an adjustable treatment aid for attaching or positioning a tool for treating a bone comprising a first frame which can be fixed to the bone, a second frame for guiding the tool and an adjusting device which allows the first frame to be spatially adjusted relative to the second frame, wherein the adjustable treatment aid includes a reference star which can be detachably attached to the second frame and further comprises a contact interface for contacting the bone which is to be treated to detect the position of the bone by scanning by contact.

US 2006/0235290 A1 discloses a method of using a surgical navigation system for positioning a medical device relative to an anatomical feature, wherein the medical device is navigated relative to the anatomical feature in a first degree of freedom, the medical device is fixed to the anatomical feature in the first degree of freedom and the medical device is subsequently navigated relative to the anatomical feature in a second degree of freedom. An embodiment shows a navigated aiming tube to define the height and axis of the hole for a pin.

US 2005/0149041 A1 discloses a system for positioning a cutting guide for preparation of a bone of a patient during total knee arthroplasty, comprising an adjustor for adjusting the cutting guide at the bone; structures operatively associated with the adjustor for adjusting the position of the cutting guide in at least one degree of rotational freedom and at least one degree of translational freedom; structures for stabilizing the adjustor at the bone; and structures for engaging the cutting guide.

US 2002/0198531 A1 discloses an apparatus for positing the cutting angle of a bone cutting guide comprising first fastening means to fasten said positioning apparatus to a bone such that all of said apparatus and cutting guide fastening means can rotate relative to the fastening axis; second fastening means to fasten said positioning apparatus at a second fastening location onto said bone, different from the first fastening location, such that said apparatus is fixed in a required position within said rotation relative to said first fastening axis; first adjusting means for adjusting the orientation of the cutting angle in rotation relative to a second axis perpendicular to said first fastening axis, wherein said orientation is known as the anterior posterior slope; and second adjusting means to adjust the height of said cutting guide relative to said positioning apparatus along the third axis perpendicular to the two previous axes, wherein said two previous axes are the fastening axis and the second axis.

US 2002/0038085 A1 of the applicant discloses a method for applying an element to a body, wherein the position of the device for preparing or producing a connection between the body and the element is detected relative to the position of the body.

In general, the usage of a fine adjustable cutting jig or block is quite complex and adds several minutes to the surgery time. If the cutting jig would be placed free hand, this would save time but would not be accurate enough to utilize the benefit of navigated surgery.

SUMMARY OF THE INVENTION

It is the object of the present invention to propose a method and device for positioning or attaching an instrument or device, such as an incision or cutting block or jig, relative to a structure, e.g. a bone, especially relative to the femur and the tibia, or relative to a joint or a part of a joint, whereby the attaching or positioning is simplified.

This object is solved by the features of the independent claims. Advantageous embodiments are defined in the dependent claims.

The present invention provides a solution to reduce time when exactly positioning and attaching a cutting jig and furthermore reduces the invasiveness compared to existing fine adjustable systems for the attachment of cutting jig, since only two pins are necessary to fixate the cutting jig. The attachment of more pins is optional.

A method for positioning and/or attaching a device or instrument, such as a cutting block or cutting jig or incision block or a ligament balancing device to a structure, such as a bone structure, e.g. the tibia or femur, or to a part of a joint, includes at least one or all of the steps mentioned hereinafter.

A positioning tool also referred to as a spoon is inserted into a joint, preferably between the elements forming the joint. Taking the knee as example, the positioning tool is inserted into the gap between the femur and the tibia. The positioning tool or spoon can be built or shaped as described in EP 07 102 301.4 of the applicant filed on Feb. 13, 2007, the teachings of this application with respect to the structure and use of the positioning tool or spoon are incorporated into this application.

The positioning tool or spoon can be formed of one part having a side or element which can be inserted into the structure or joint and having a second part which serves as holding or connection structure to be connected to the instrument or jig. This first part is hinged to the second part, wherein the hinge or articulation can be formed of a malleable or plastic material. Preferably, the hinge is formed by a plastically deformable part of the positioning tool which has a shape that can manually be changed and which basically retains the shape when no external force is acting on the hinge. As a further embodiment the hinge can be formed as a ball joint or swivel joint. The ball joint or swivel joint is preferably self-inhibiting or self-locking so that after changing the position of the joint, the adjusted position can be maintained by the joint itself without the need to further lock the adjusted position. Such a hinge can e.g. be used to adjust the slope of a jig connected to the spoon being inserted in a joint, e.g. the knee.

The device or instrument e.g. a cutting jig, to be positioned or to be attached to the structure or bone is provided. Preferably the device is pre-calibrated, so that the dimensions of the device or jig are known to the navigation software used in connection with the present invention. Advantageously, the device is connected to, e.g. directly or via a mount, or comprises at least one reference element or reference array, such as an array of three, four, or more reflecting markers which can be detected by a known navigation system, such as the VectorVision® system of the applicant. Preferably, the markers have a fixed spatial relationship with respect to the device. Thus, the user preferably does not have to register the device or jig, since the reference array is preferably fixed in a defined position relative to the device or jig.

The navigation software preferably can access input data defining the structure at which the device should be attached or positioned. Data describing the structure can for example be 3D data obtained from a CT scan or MR scan or using a pointer. Additionally, the dimension of the instrument or jig are known to the software, so that the exact distance from a guiding structure, such as e.g. a cutting slot and/or pin holes, to e.g. a reference array connected to the jig can be calculated.

Advantageously, the intended position of the device, e.g. the cutting jig, relative to the structure or bone is determined by a planning software. This relative position can be determined either directly or can be calculated using a given desired position of a part of an artificial implant defining the resection plane(s) thus defining the position of the device or jig at the structure or bone. Preferably the computer software associated with the surgical navigation system is pre-programmed to know the position of the cutting plane of the cutting jig relative to the position of the markers connected to the jig.

The device or instrument, e.g. the jig, is rotatably attached to the positioning tool or spoon. It is possible to attach the device to the positioning tool before, during or after placing the positioning tool relative to the structure, e.g. inserting the positioning tool into the gap of a joint. The device should preferably be pivotable or rotatable with respect to an axial direction of the spoon, for example in the varus and valgus direction, when the positioning tool is inserted into the knee.

The device or jig is then rotated around a first rotation axis determined by the positioning tool and preferably by a longitudinal axis of the positioning tool until a desired or correct position is reached. The desired or correct position can be determined by the navigation software showing a surgeon e.g. how far the device should be rotated in the varus or valgus direction so that the device is getting in the correct position. The device can also be part of the jig or vice versa. For example a guiding surface of the jig can be a surface of the positioning device.

Thereafter the device is at least partly attached or fixed to the structure or bone in the desired correct position. Attaching or fixing the device to the structure can be done by placing a fixing element, such as a pin, screw, Kirschner wire or any other element, into the structure, wherein this fixing element is for example guided through a first opening or hole in the device. Preferably the opening or hole in the device is located on an opposite end relative to the side or end where the device is connected to the positioning tool or spoon.

Once the device is fixed preferably by using a single fixing element, a second rotation axis of the device with respect to the structure is defined, e.g. by the longitudinal axis of the fixing element or pin. Preferably the second rotation axis is in parallel to the first rotation axis determined by the positioning tool.

Thereafter the connection between the positioning tool and the device can be loosened and optional the positioning tool can also be removed from the structure.

The device or jig is thereafter rotated around the second axis determined by the inserted fixing element until a correct position defined and showed for example by the navigation system is reached.

In this position a second fixing element, such as for example a pin, can be inserted into the structure, which fixing element is preferably guided by a second opening or hole in the device.

Thus, the device is attached to the structure in the desired position as given e.g. by the navigation system by two fixing elements.

Optionally, a third and a fourth or even more fixing elements or pins can be inserted to securely attach the device to the structure.

Thus, placing a device or a jig at a structure or a bone can be simplified, especially by using a positioning tool as a "third hand".

In one embodiment the device or jig can be fine adjusted as set forth in the description of the device for attaching or positioning a jig in this application.

According to a further aspect the invention relates to a device for positioning an instrument, e.g. a jig, such as a cutting jig or a drilling jig, at a structure, such as a bone, using at least one fixing element, such as a pin, screw or Kirschner wire. The device comprises further at least one adjusting element, such as a (hand) screw which interacts and preferably directly interacts with the fixing element, such as a pin, and which interacts with, or is connected to, the instrument or jig to be positioned. The device can also be part of the jig or vice versa. For example a guiding surface of the jig can be a surface of the positioning device. The adjusting element can preferably directly be in contact with the fixing element or pin, so that no device or structure has to be positioned between the adjusting element and the fixing element, which simplifies the structure. The adjusting element is preferably provided in a way that the relative position between the fixing element or pin and the jig can be adjusted by changing the position of the adjusting element, such as for example by rotating and/or shifting the adjusting element with respect to the fixing element and/or with respect to the jig.

A system to position an instrument or jig comprises the above described device and a positioning tool or spoon.

The adjusting element preferably comprises at least one opening, hole or through boring for guiding the fixing element or pin within the adjusting element. Advantageously, the hole within the adjusting element is not in a concentric position of or within the adjusting element, but is provided in an excentric position of or within the adjusting element. Preferably the hole or boring or the center axis thereof is offset compared to a center axis of the adjusting element. As a consequence, when the adjusting element is moved or rotated around the fixing element, the device or jig within which the adjusting element is supported, positioned or mounted or which is part of it, can be displaced with respect to the position of the fixing element, so that a fine adjustment of the device or jig is possible by turning or moving the adjusting element without having to alter the position of the fixing element.

Preferably the adjusting element is made in one piece and comprises no moveable parts. Thus, fine adjustment of the jig is possible without changing the shape of the adjusting element itself.

The adjusting element is preferably formed as an excentric bushing.

Advantageously, the device or jig comprises a connection structure for at least one marker or a reference array comprising a defined number of markers.

According to a further aspect the invention is directed to a method for positioning an instrument, such as a jig, using at least two movable or rotatable adjusting elements, such as excentric bushings. The position of the instrument or jig relative to at least two fixing elements which are guided by or located within the at least two adjusting elements can be changed or adjusted by actuating one or two of the adjusting elements. Preferably the relative position of the instrument or jig compared to at least one fixing element is changed in at least a first degree of freedom, if the adjusting elements are moved or turned in the same direction. For example the instrument or jig is moved up and down with respect to the fixing elements if those adjusting elements being excentric bushings are turned with the same speed in the same direction. Although a shift in a lateral direction can occur, this does not affect the alignment of the reference plane for cutting defined by the cutting jig.

If the adjusting elements are moved or turned in different or opposite directions, the position of the instrument or jig with respect to the fixing elements is changed in a second different degree of freedom, e.g. in the case of a femur or tibia being the structure in which the fixing elements are inserted, in the varus or valgus direction. The same effect can be achieved if only one adjusting element is moved or turned or if the adjusting elements are moved or turned with different speeds.

The invention will be further explained by reference to the accompanying drawings:

FIGS. 8a to 8f show embodiments of a positioning tool having a hinge;

FIGS. 10a to 10e show the positioning device in various adjusting positions;

FIG. 11 is a rear-view of the positioning device shown in FIG. 9; and

FIG. 12 is a cross-sectional view of the positioning device of FIG. 11 along line A-A.

Figure 1:
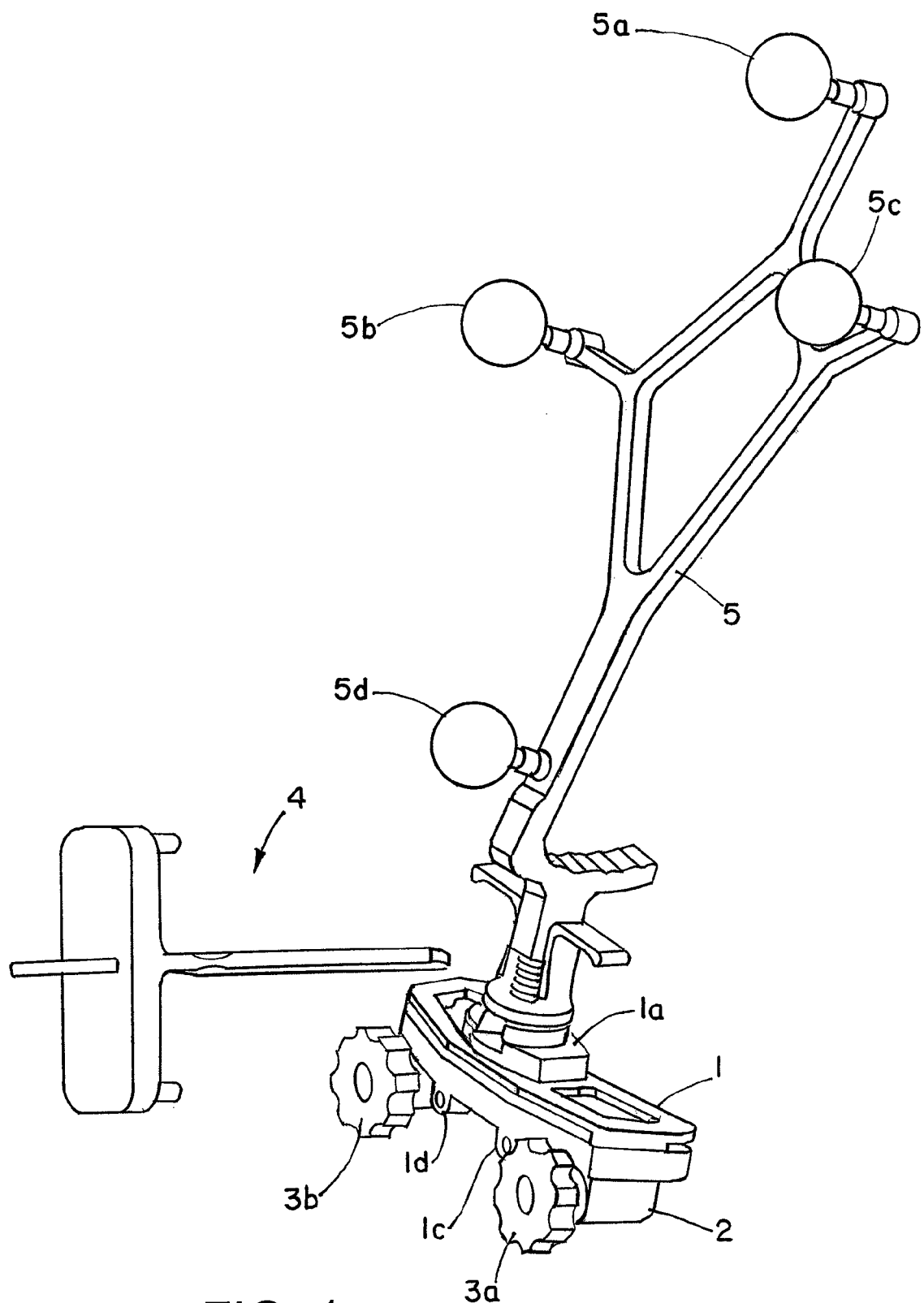
FIG. 1 shows an embodiment of a system for positioning a cutting jig.

FIG. 1 shows an embodiment of a system for positioning an instrument, namely a cutting jig, at a knee. The system comprising at least one positioning device 2 connected to or integrated into the cutting jig 1, a positioning tool 4 also referred to as "spoon" and a reference array 5 having four reflective markers 5a to 5d being spheres. The position of the reference array 5 can be determined by a navigation system.

The reference array 5 is detachably attached to the jig 1 in a fixed manner so that no relative movement or rotation can occur between the reference array 5 and the jig 1.

Figure 2A:
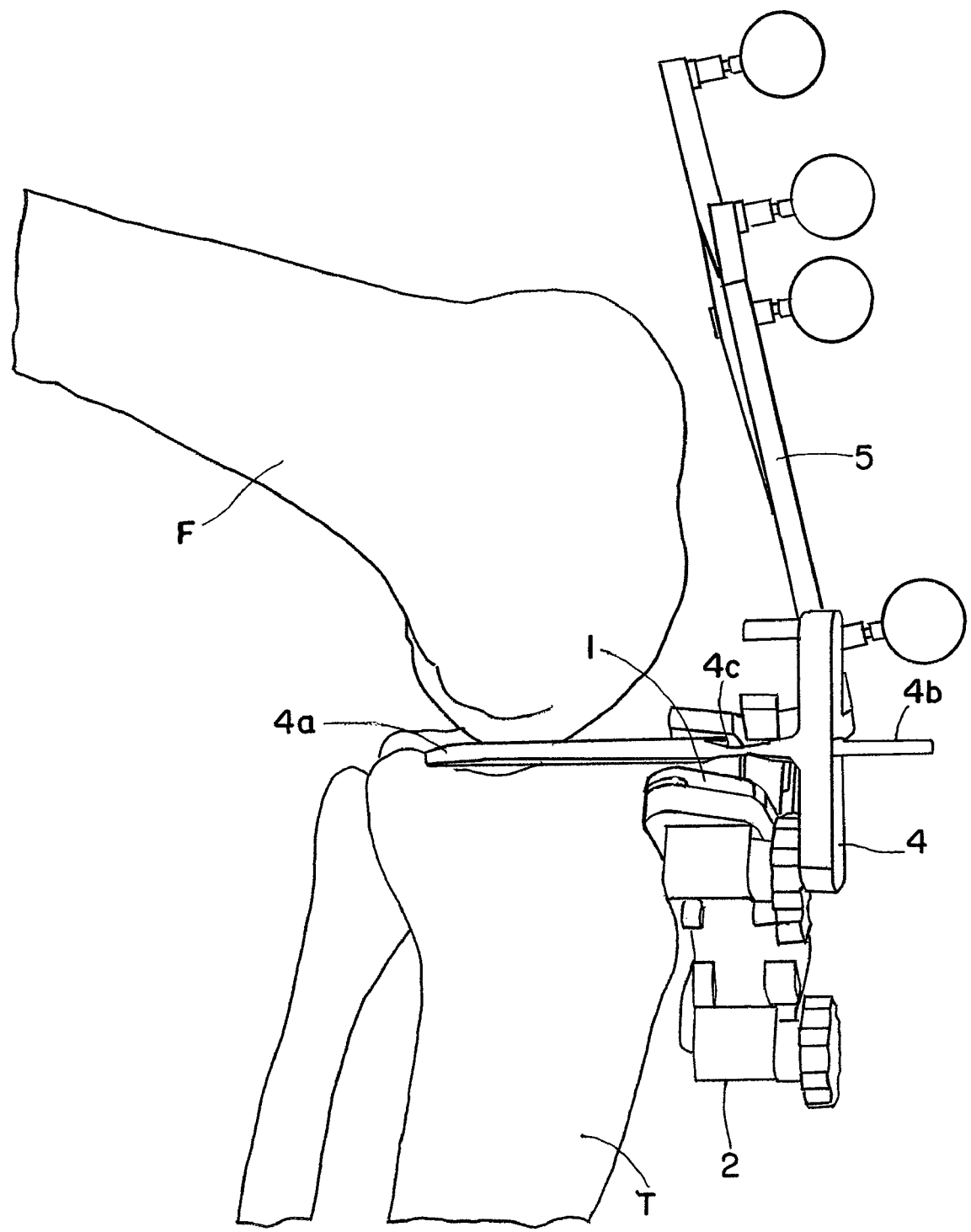
FIG. 2a shows the system of FIG. 1, wherein the device for positioning the cutting jig is connected to a spoon which is inserted into the gap of a knee joint.

The cutting jig 1 or positioning device 2 is pivotably or rotatably attached to the positioning tool 4, as shown in FIG. 2a.

Figure 2B:
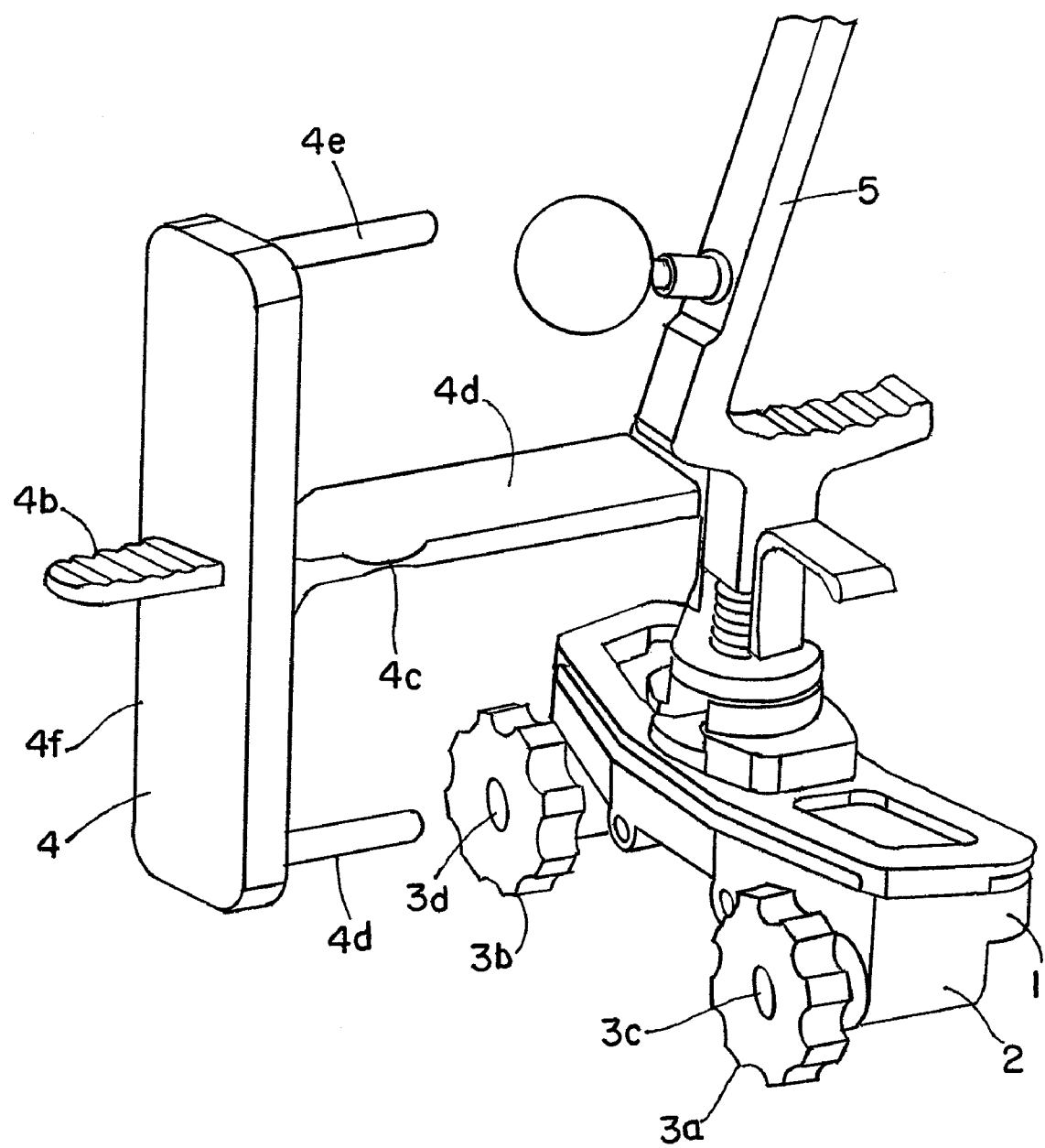
FIGS. 2b and 2c show how the device for positioning the cutting jig is connected to the spoon.

FIG. 2b shows that the positioning tool 4 comprises two connecting elements or pins 4e and 4d which are extending from the base plate 4f of the positioning tool F in a substantially vertical direction. Preferably the longitudinal axis of the pins 4e and 4d is parallel to the longitudinal axis of the front part 4a of the positioning tool 4. Advantageously, the diameter of pins 4d and 4e of the positioning tool 4 is substantially the same as that of pins 6 used to fix the positioning device 2 to the tibia T. Further advantageously, this diameter of pins 4e, 4d and 6 is basically the same or a little less than the inner diameter of the openings or through holes 3c and 3d of adjusting elements 3a and 3b. As shown in FIG. 2b, one pin 4d of the positioning tool is inserted into an opening or through hole 3d of an adjusting element 3b, so that the positioning device 2 in which the adjusting element 3d is provided is pivotably connected to the positioning tool 4. The positioning device 2 and the cutting jig 1 are movable around the axis determined by the middle axis of pin 4d.

Figure 2C:
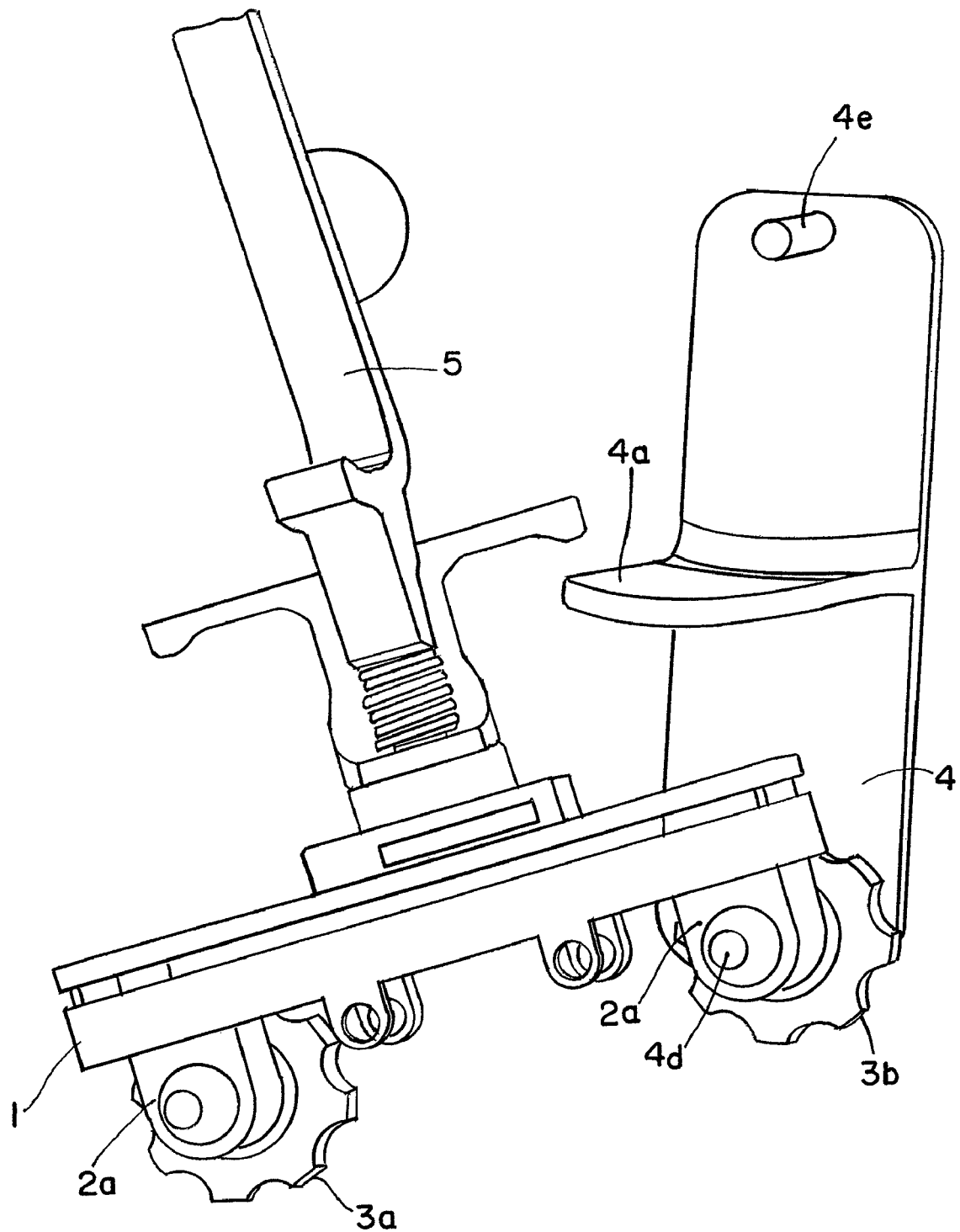

FIG. 2c shows the situation where the positioning tool 4 shown in FIG. 2b supports the positioning device 2 together with the cutting jig 1. It is noted that the positioning device 2 shown in this embodiment comprises two positioning elements 2a and 2b.

The front part 4a of the positioning tool 4 is inserted into the knee, namely into the gap between the femur F and tibia T, to roughly position and hold the jig 1. The jig 1 is rotatively connected to the positioning tool 4 thus defining a first rotation axis. The slope can be adjusted by turning the joint 4c of the positioning tool 4, for example by moving the part 4b of the tool 4 while the opposite part 4a being inserted into the knee basically remains in position. The navigation system can determine and show the correct slope for resection when using a pre-calibrated jig 1.

Figure 3:
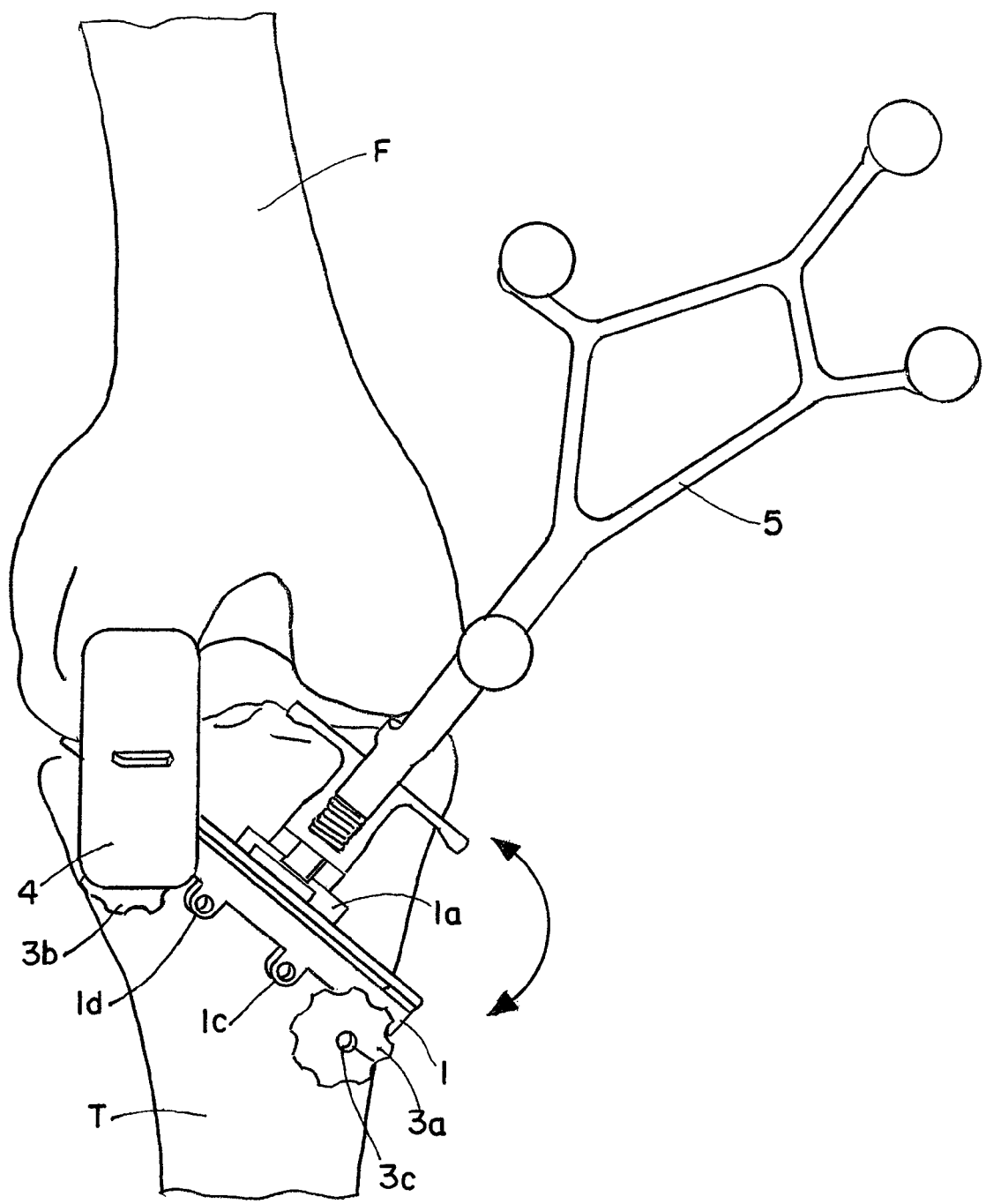
FIG. 3 shows that the jig is rotated to a calculated position.

As shown in FIG. 3, the jig 1 can be rotated in the varus/valgus direction as indicated by the arrow in FIG. 3. The centre of rotation is determined by the connection between the jig 1 and the positioning tool 4. As soon as the jig 1 and the positioning tool 4 are in the position shown in FIG. 3, the navigation software shows the user how to rotate the jig 1, so the free hole 3c being in the first adjusting element 3a is brought into the correct position, as e.g. shown and determined by the navigation software.

Figure 4:
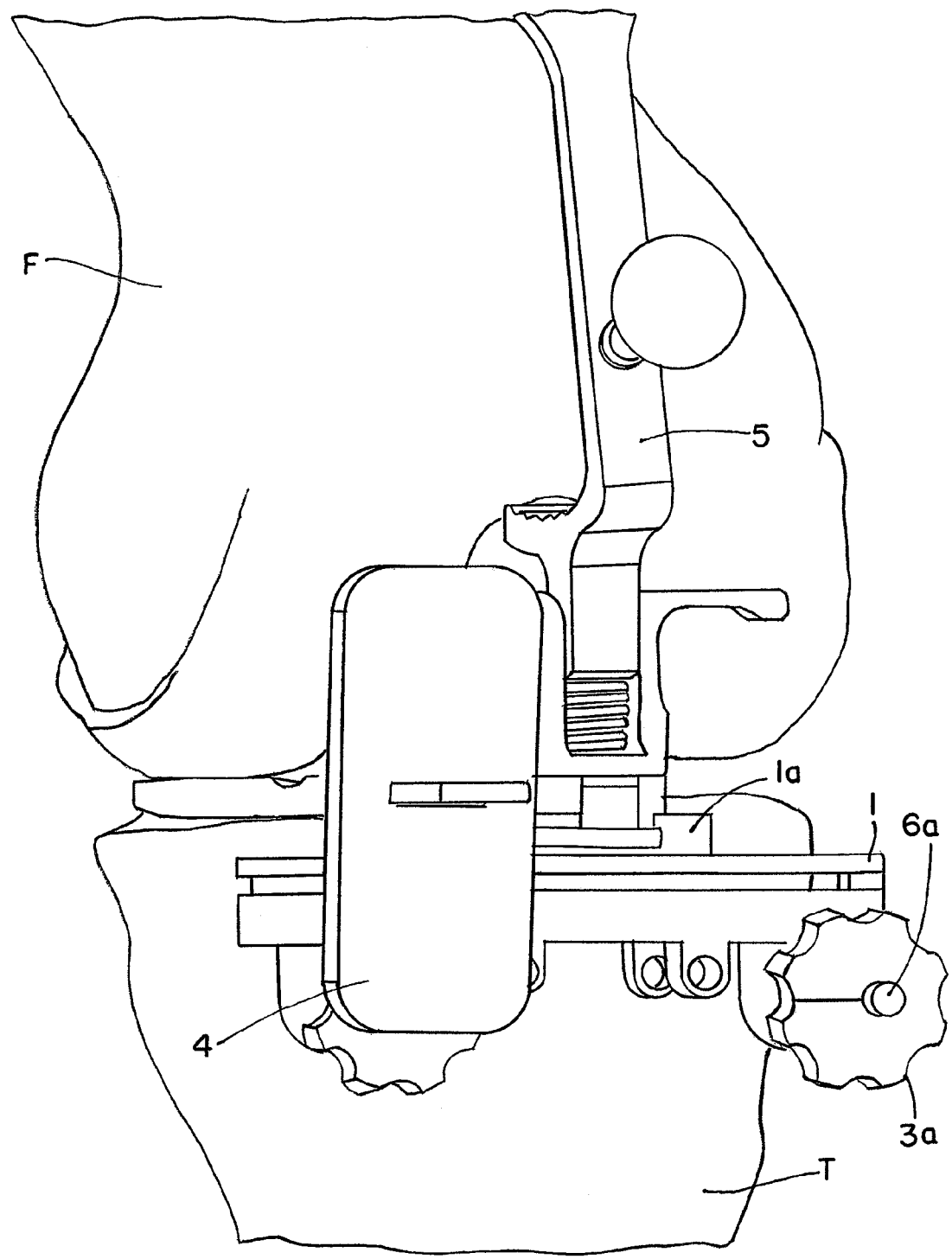
FIG. 4 shows the device with a first pin inserted.

FIG. 4 shows the jig 1 after being brought into the correct position. A first pin 6a is inserted through the adjusting element or screw 3a into the bone T lying behind the adjusting element 3a. Thus, the slope of the jig 1 is locked or fixed and a second centre of rotation for adjusting the varus/valgus angle is defined by the axis of pin 6a.

Figure 5:
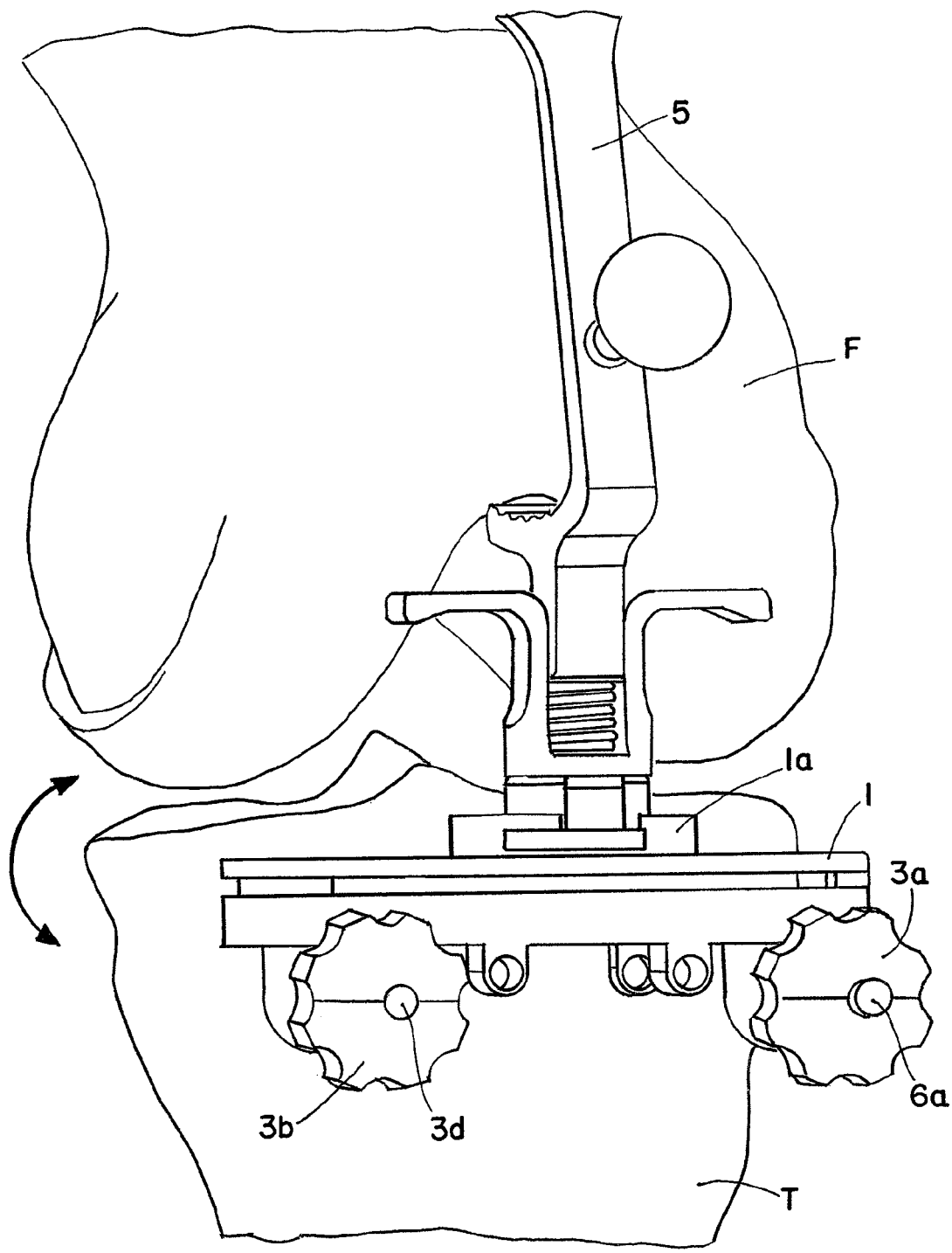
FIG. 5 shows the device of FIG. 4 detached from the spoon and rotated around the first pin.

As shown in FIG. 5, the positioning tool 4 is removed, so that the jig 1 can be rotated around the first pin 6a being now the centre of rotation. The navigation software can show the user how to navigate a second free hole 3d being within the second adjusting element 3b into the correct position.

Figure 6:
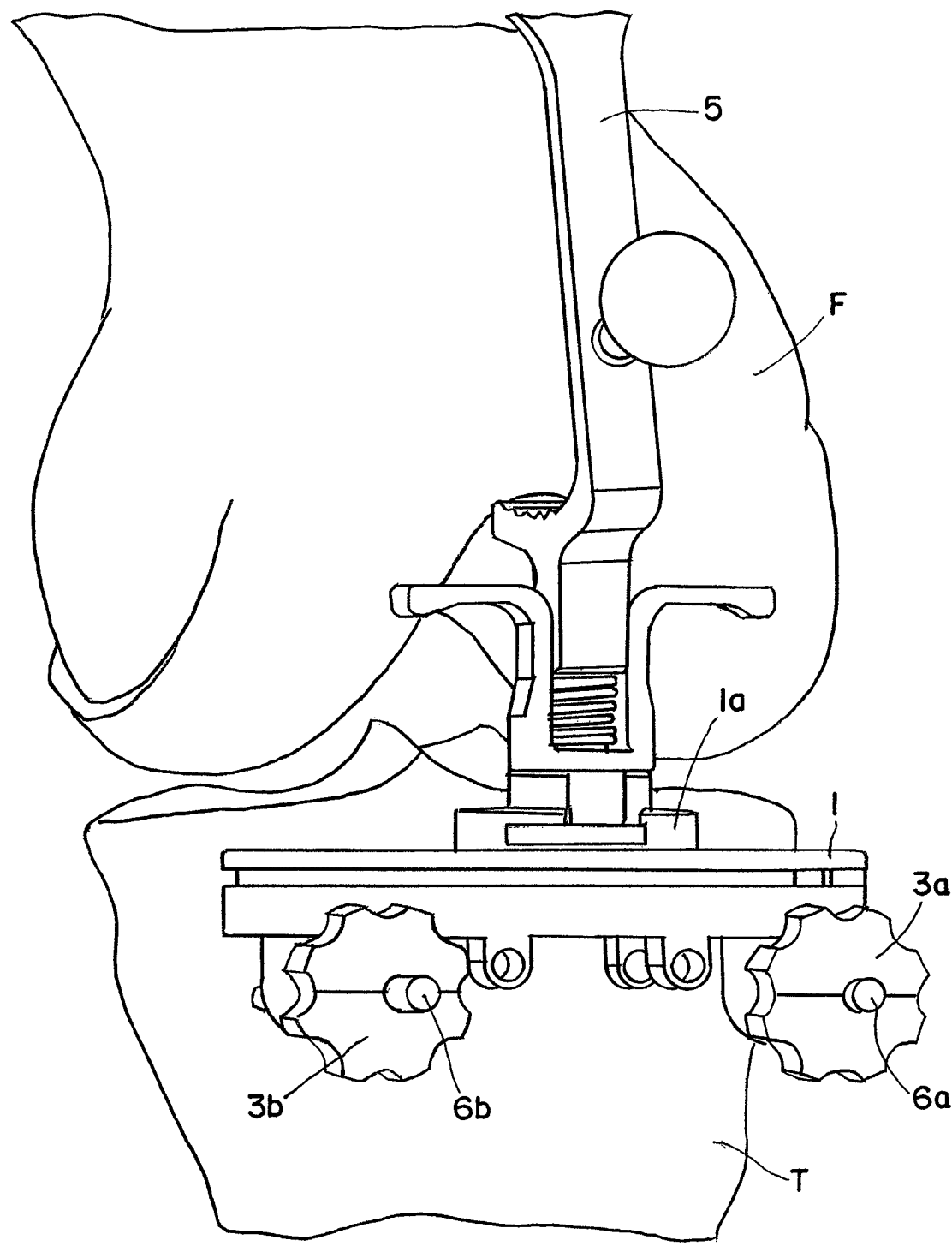
FIG. 6 shows the device of FIG. 5 with a second pin inserted.

After the correct position of the jig 1 is reached, the user inserts the second pin 6b to lock or fix the resection height and the varus/valgus angle at the same time, as shown in FIG. 6.

Figure 7:
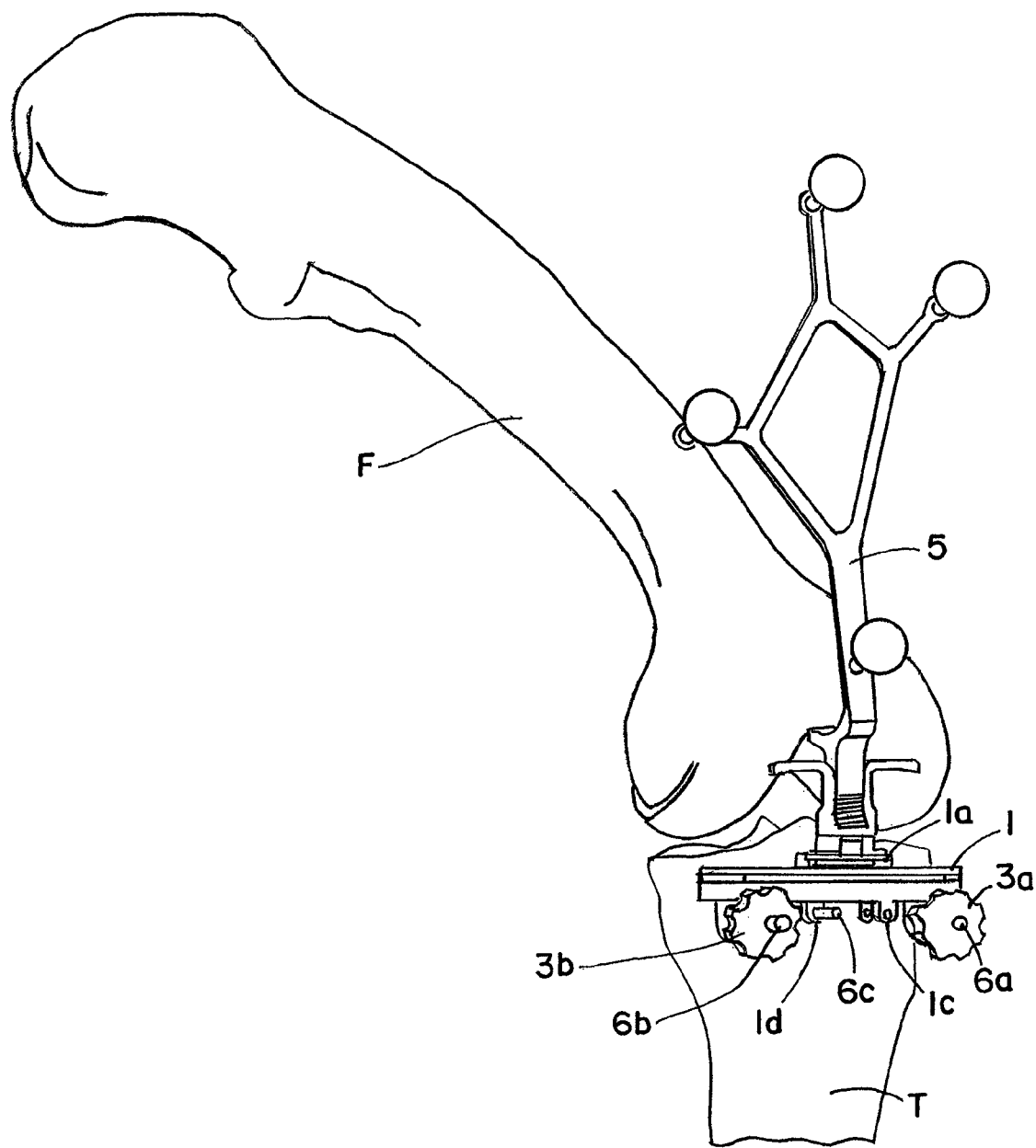
FIG. 7 shows the device of FIG. 6 to be adjusted and fixed by a third pin.

As shown in FIG. 7, the user can finally fix the jig 1 in all degrees of freedom by inserting one or more further pins 6c trough guides or holes 1c, 1d in the positioning device or jig 1 into the bone T to provide a stable connection between the bone T and the jig 1.

FIGS. 8a to 8f show different embodiments of the positioning tool 4 having respective different joints 4c. One side 4a of the positioning tool 4 is for inserting into a joint, as shown in FIG. 2. The opposite side 4b serves as connecting element for attaching the jig 1 rotatively to the positioning tool 4.

FIG. 8a shows a first embodiment of the positioning tool 4, wherein the joint 4c is formed as integral part of the positioning tool 4. The joint 4c can for example be a portion of the element 4a, or 4b, so that it is possible to bend one part 4b of the tool 4 with respect to the other part 4a by bending the joint 4c between the parts 4a and 4b. Preferably the material used for forming the positioning tool 4 or for forming the joint 4c is plastically deformable or malleable, so that after the joint 4c is deformed, joint 4c remains in the deformed position.

Figure 8B:
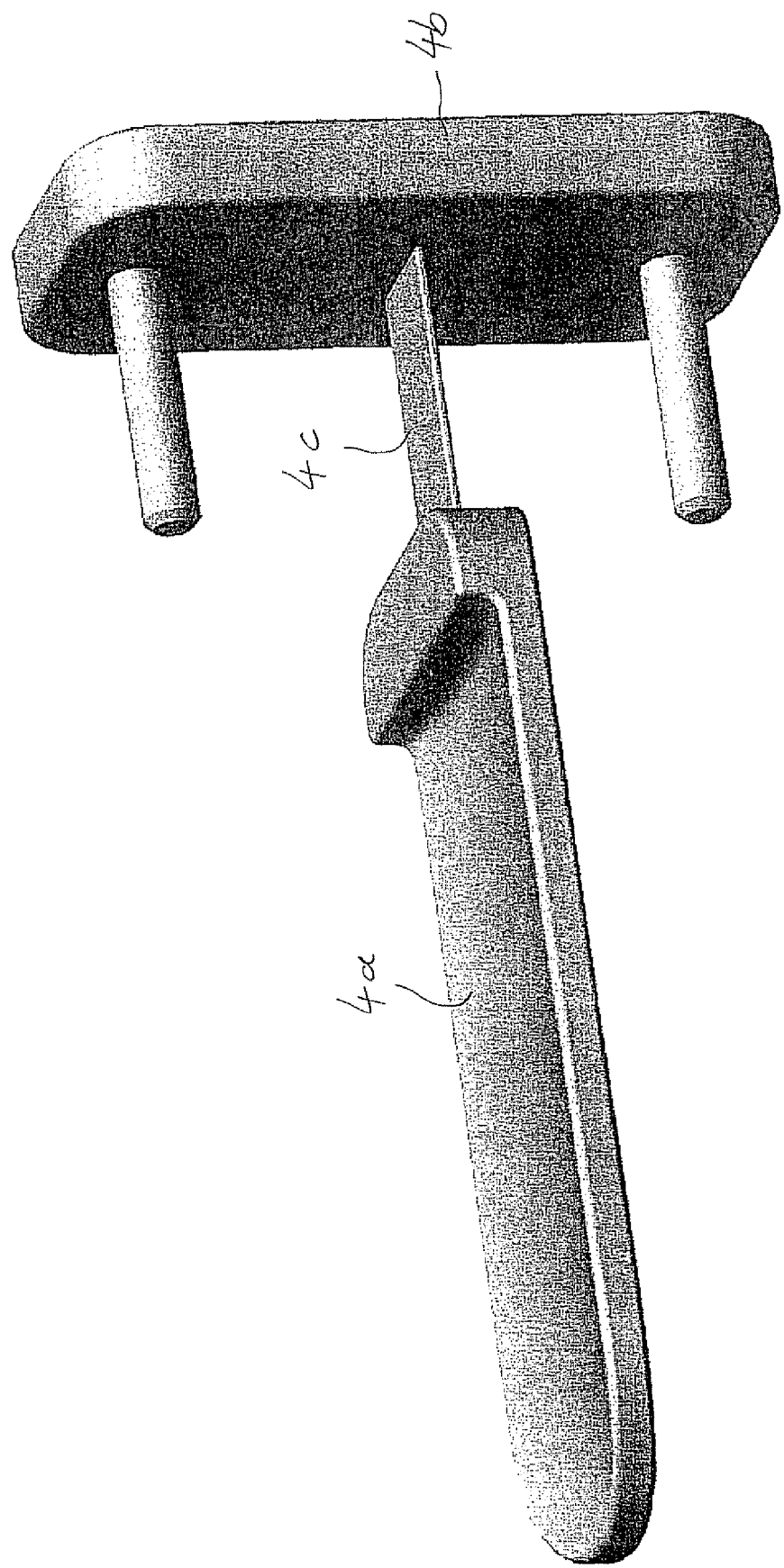

FIG. 8b shows a second embodiment of the tool 4, wherein the front part 4a is connected to the part 4b by a thin plate, such as e.g. a thin metal plate, which is deformable.

FIG. 8c shows a third embodiment similar to the second embodiment, wherein the thin plate 4c is replaced by a thin member or wire 4d being deformable and able to retain the deformed position.

Figure 8D:
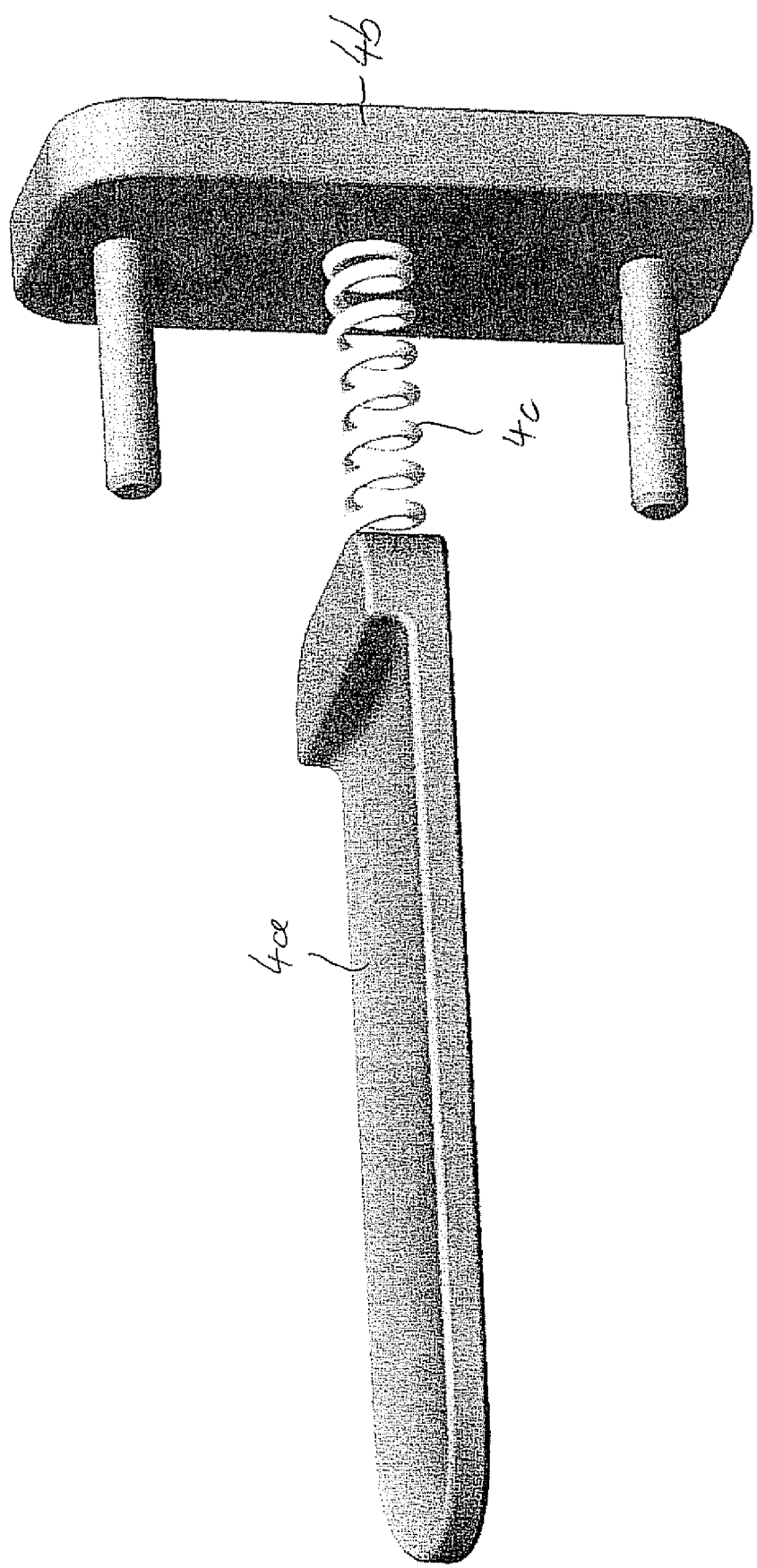

FIG. 8d shows a forth embodiment, wherein the joint 4c positioned between elements 4a and 4b is formed by a deformable spring.

FIGS. 8e and 8f show two embodiments of the tool 4, wherein the joint 4c is formed by a swivel joint, as shown in FIG. 8e, and a ball joint, as shown in FIG. 8f, respectively. Preferably both joints are self-locking.

Figure 9:
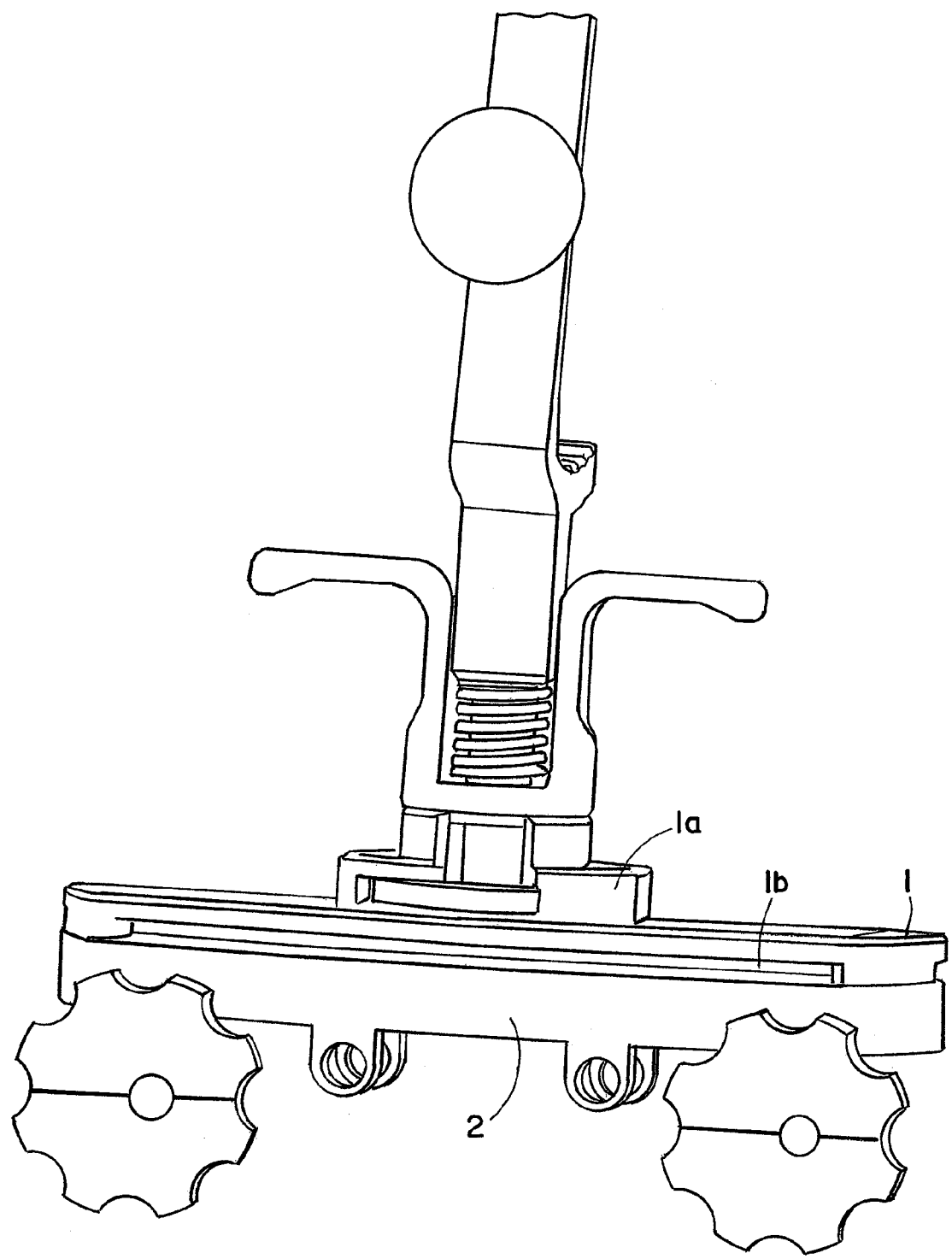
FIG. 9 shows the positioning device in home position.

FIG. 9 shows the jig 1 attached to the positioning device 2 in home position.

Figure 10A:
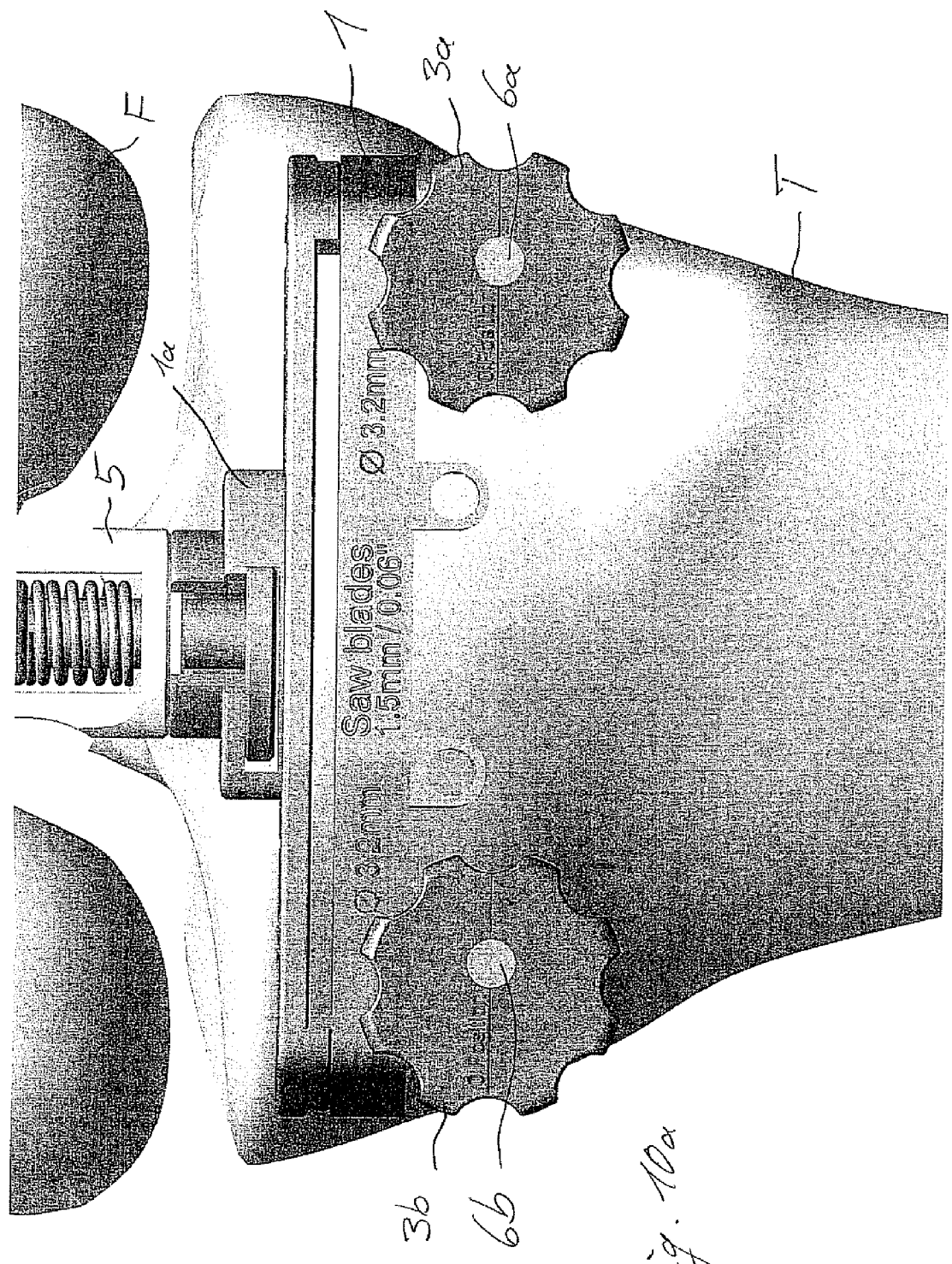

FIG. 10a shows it attached to a bone T by means of pins 6a and 6b. As indicated by the line "0 Position" on each of the adjusting elements 3a and 3b, both adjusting elements 3a, 3b are in the home position.

FIG. 10b shows the device of FIG. 10a, wherein both adjusting elements 3a and 3b are turned by 90 degrees counterclockwise, which results in lowering the jig 1 with respect to the bone T shown as downward movement of the jig 1 in FIG. 10b compared to the position of the jig 1 in FIG. 10a.

Figure 10C:
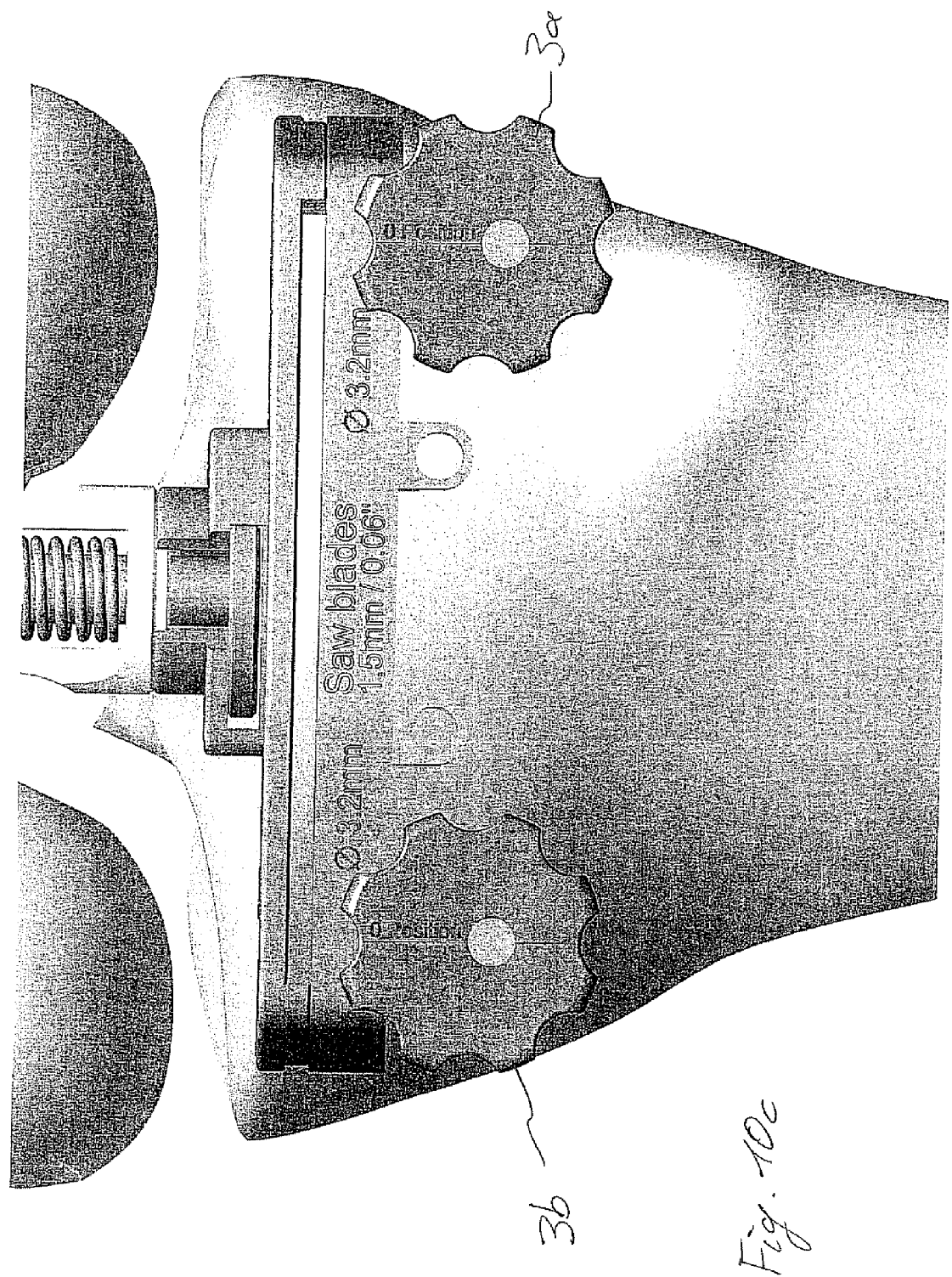

FIG. 10c shows a situation where both adjusting elements 3a and 3b are turned clockwise by 90 degrees starting from the home position shown in FIG. 10a resulting in the lifting of the jig 1 with respect to the home position shown in FIG. 10a.

Figure 10E:
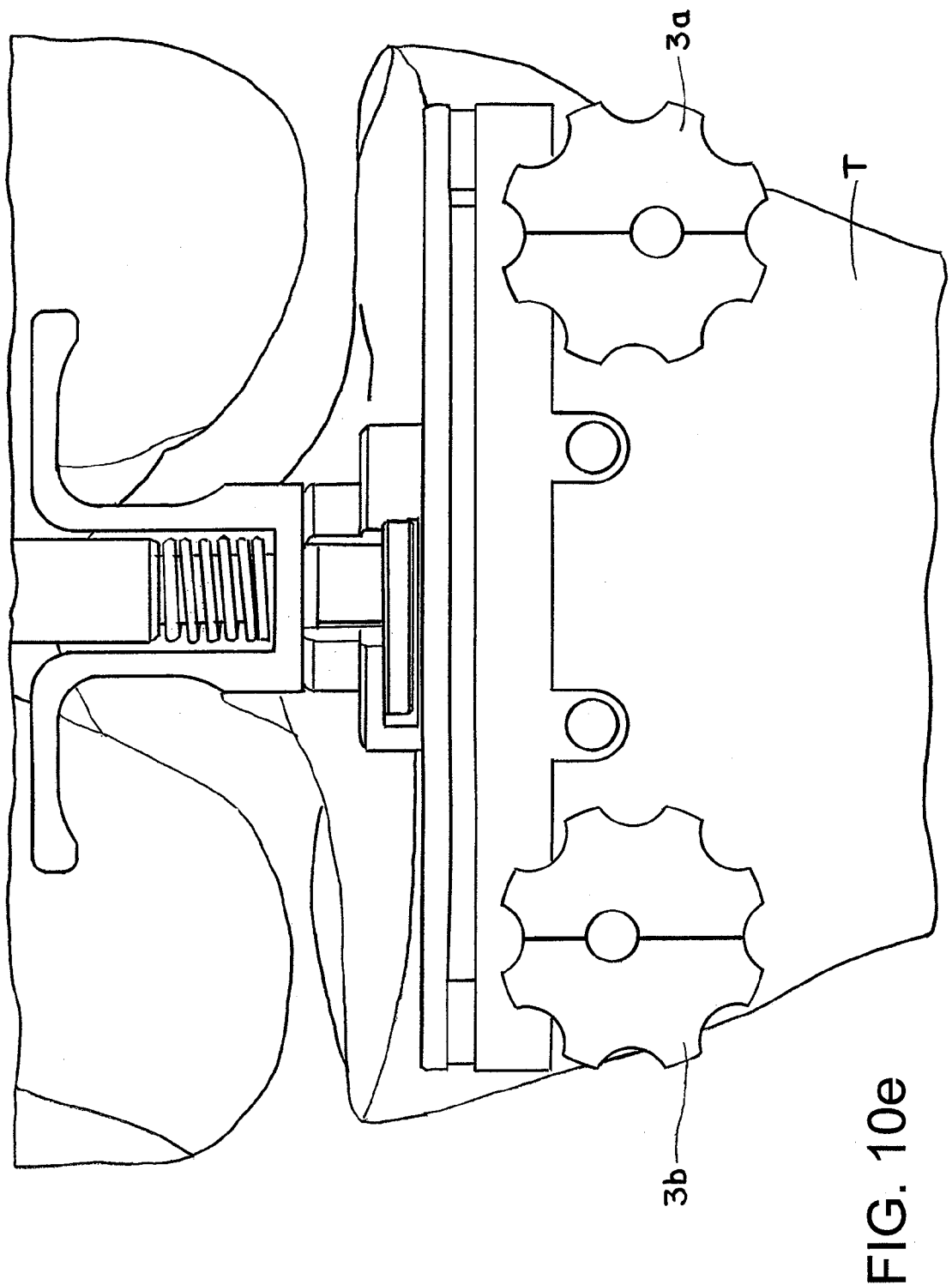

If both adjusting elements 3a and 3b are turned in the same direction, as shown by the examples of FIGS. 10d and 10e, the jig 1 defining the resection plane can be adjusted with respect to the resection height.

FIG. 10d shows a situation where starting from the home position of FIG. 10a one adjusting element 3a is turned by 90 degrees in a counterclockwise direction and the other adjusting element 3b is turned by 90 degrees in a clockwise direction, resulting in a chance of the varus/valgus angle. As shown in FIG. 10d, the jig 1 is turned clockwise with respect to the bone T.

FIG. 10e shows a situation where starting from the home position of FIG. 10a one adjusting element 3b is turned by 90 degrees in a counterclockwise direction and the other adjusting element 3a is turned by 90 degrees in a clockwise direction, resulting in a chance of the varus/valgus angle. As shown in FIG. 10e, the jig 1 is turned counterclockwise with respect to the bone T.

FIG. 11 shows a rear-view of the jig 1 having the positioning device included comprising the adjusting elements 3a and 3b and the bearings 7a and 7b for the adjusting elements.

The jig 1 comprises a connection structure 1a for connecting the reference array 5 and a slot 1b serving as a guide for a cutting blade.

The jig 1 further comprises two holes 1c and 1d serving as guides for further pins 6c to be inserted, as shown in FIG. 7.

As can be seen in FIG. 12 being a cross sectional view along line A-A in FIG. 11, an adjusting element 3a or 3b is formed as a screw having a centre axis $C_S$ within the screw 3a and extending parallel to the centre axis $C_S$ a hole 3c is formed having a centre axis $C_H$, wherein the centre axis $C_H$ is offset by a distance d from the centre axis $C_S$. If a pin 6a is inserted trough the hole 3c to be fixed into a bone T, as shown in FIGS. 4 to 7, the adjusting element 3a is in direct contact with or guides the fixing element 6a. If the adjusting element or screw 3a is turned, the center of rotation is the center axis $C_H$ of the hole 3c, if the diameter of the pin 6a is about or little less than the diameter of the hole 3c. Since the hole 3c is excentric within the adjusting element 3a, since the center axes $C_H$ and $C_S$ are displaced, movement of the adjusting element 3a leads to lifting or lowering of the jig 1, so that the position of at least one side of the jig 1 and thus the position of the slot 1b defining the resection plane can be adjusted.

The invention claimed is:

1. A method for positioning and/or attaching a device to a patient, the device comprising first and second rotatable adjusting elements supported with respect to the jig for rotation about respective axes, the first and second adjusting elements each including an excentric bushing having a center axis offset from the respective axis of the respective adjusting element, and first and second fixing elements extending through the excentric bushings of the first and second adjusting elements respectively and attached to the body of the patient, the fixing elements being rotatably constrained within the respective excentric bushing, comprising the steps:
   (a) providing a pre-calibrated device connected to or bearing a reference array;
   (b) inserting a positioning tool into a joint space between a first bone and a second bone of the patient;
   (c) rotatably attaching the device to the positioning tool;
   (d) rotating the device around a second rotation axis determined by the positioning tool;
   (e) fixing the device to the patient thereby defining a first rotation axis by inserting the first fixing element through a first one of the excentric bushings;
   (f) rotating the device around the first rotation axis by rotating the device around the first fixing element;
   (g) fixing the device to the patient via a fixing point which is not on the first rotation axis by inserting the second fixing element through a second one of the excentric bushings; and
   (h) rotating the first and second adjusting elements uniformly to effect translating movement of a resection plane of the jig, and rotating at least one of the first or second adjusting elements non-uniformly with respect to the other to effect rotating movement of the resection plane of the jig.

2. The method according to claim 1, wherein after step (e) and before step (f) the method comprises the step:
   (e1) loosening the connection between the device and the positioning tool.

3. The method according to claim 1, wherein a fixing step is performed by inserting a pin.

4. The method according to claim 1, wherein the positioning tool is removed after a connection to the device is loosened.

5. The method according to claim 1, wherein a slope of the device is adjusted by turning a swivel joint of the positioning tool.

6. The method according to claim 1, wherein a navigation system determines a rotation angle in step (e) and/or in step (g) and/or a slope of the device.

7. The method according to claim 1, wherein the reference array is trackable by a medical navigation system.

* * * * *